Figure 1A:
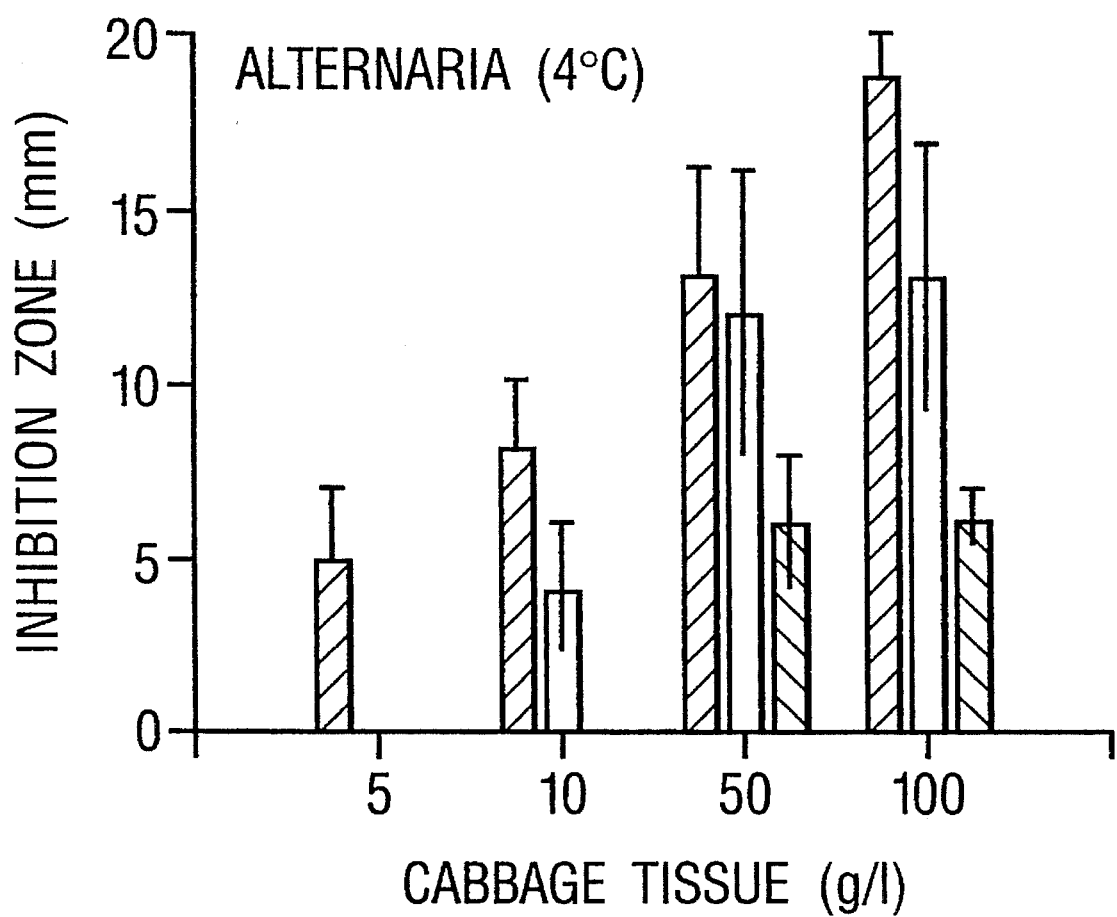
Figure 1C:
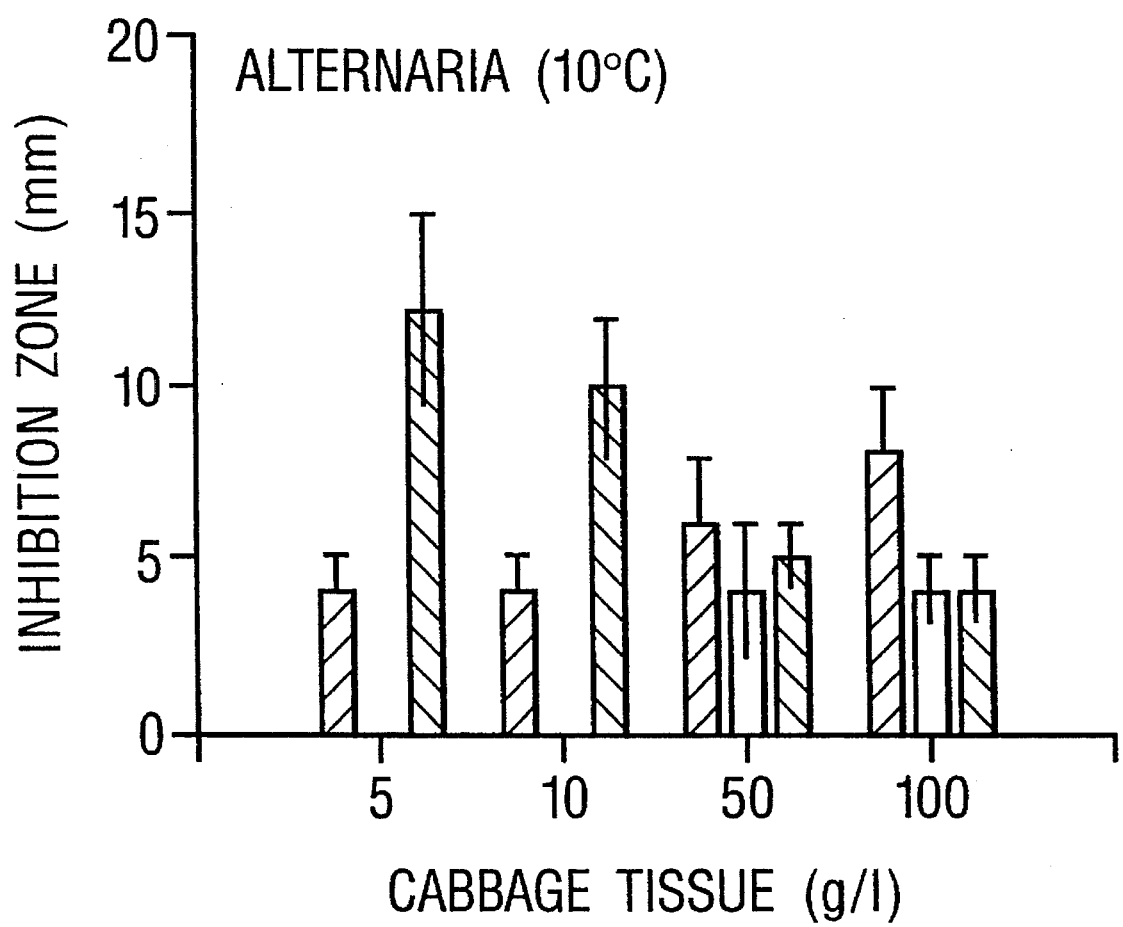
Figure 1D:
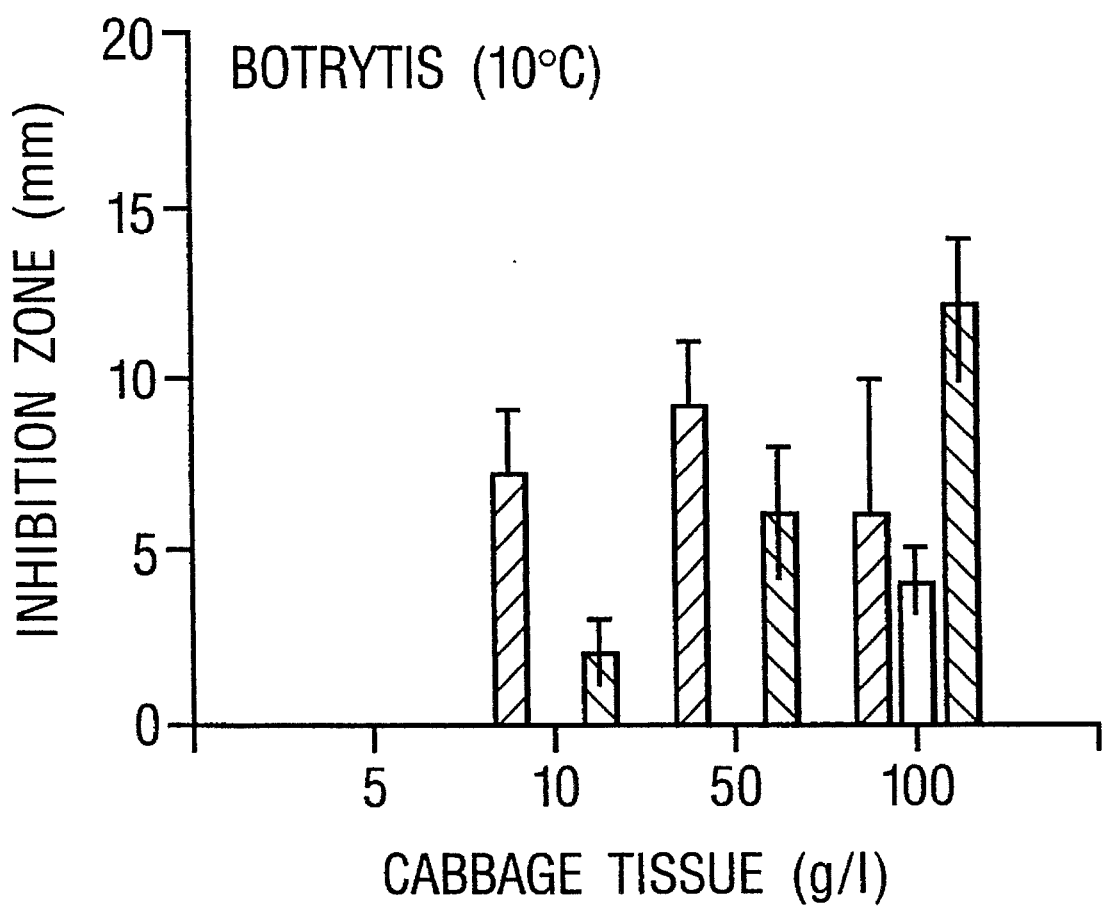
Figure 2A:
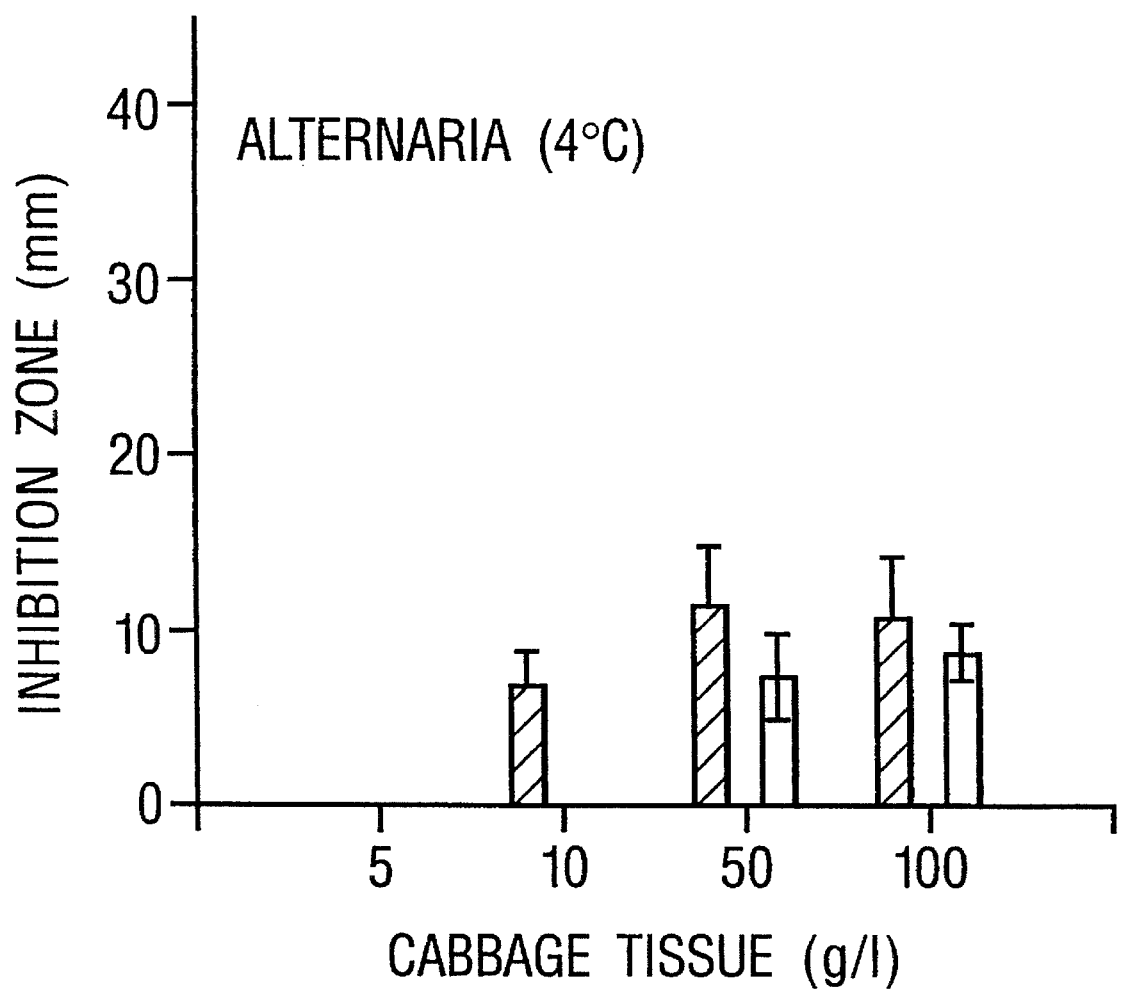
Figure 2B:
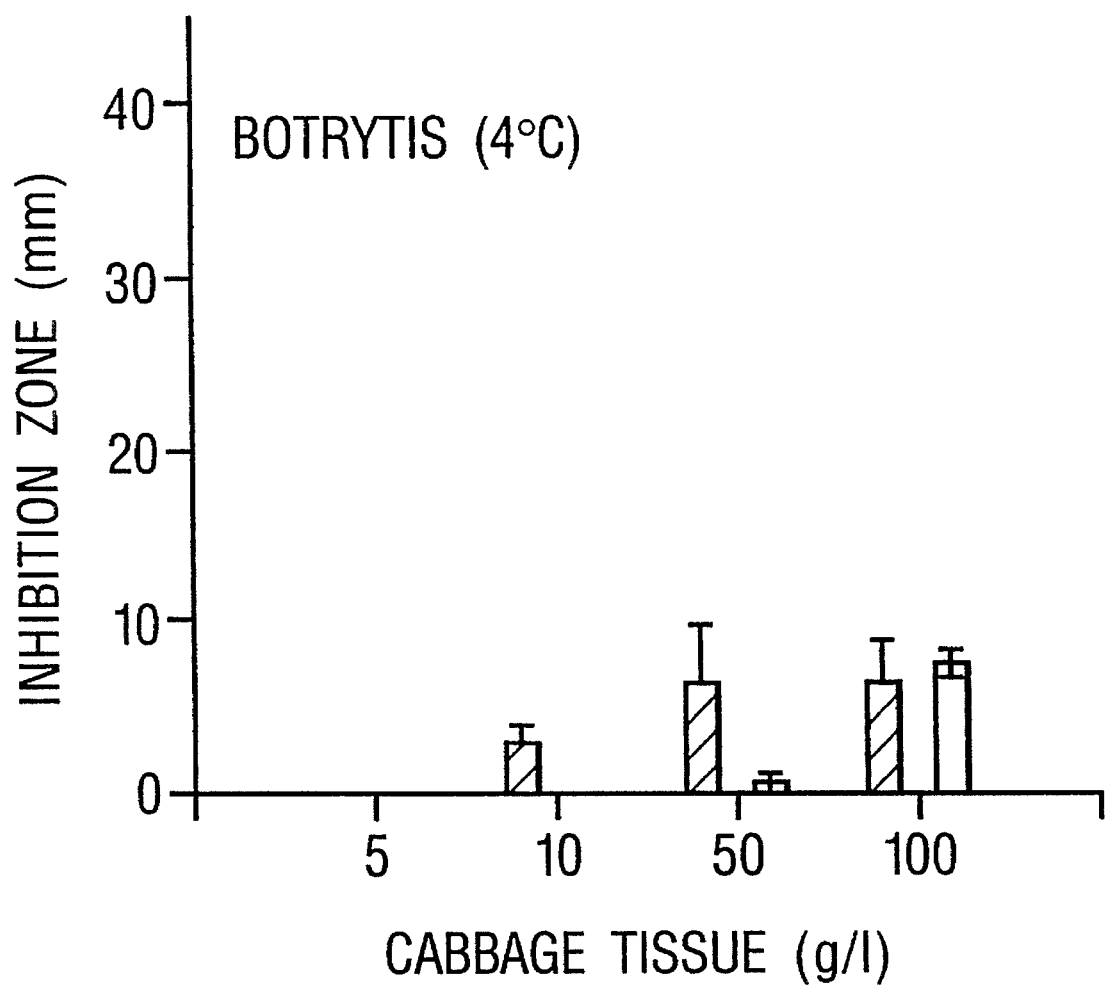
Figure 2C:
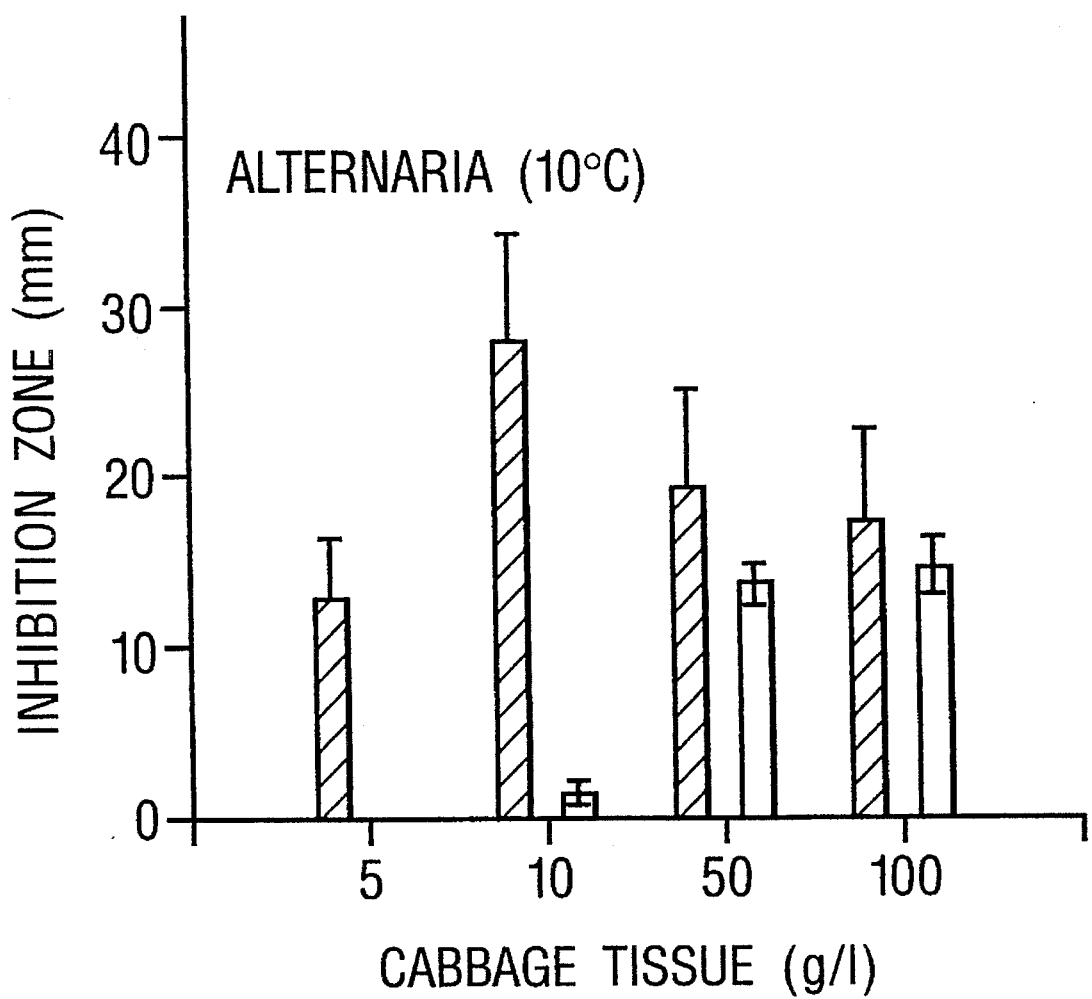
Figure 2D:
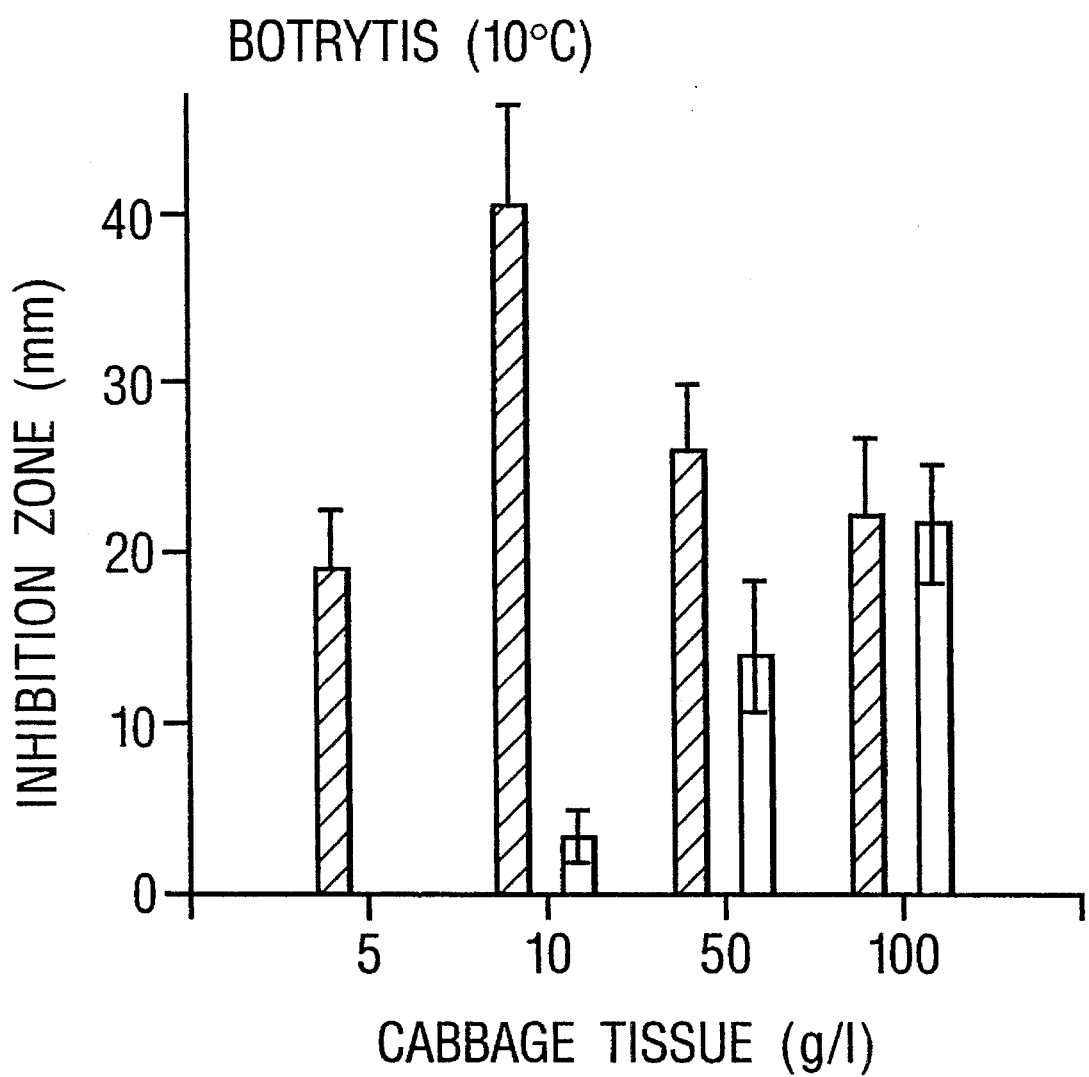

United States Patent [19]

Leifert et al.

[11] Patent Number: 5,597,565
[45] Date of Patent: Jan. 28, 1997

[54] ANTIBIOTICS FOR BIOLOGICAL CONTROL OF POST HARVEST DISEASES

[75] Inventors: Carlo Leifert, Aberdeen; Harold A. S. Epton, Cheadle; David C. Sigee, Sale, all of United Kingdom

[73] Assignee: The Secretary of State for Ministry of Agriculture, Fisheries & Food in her Britannic Majesty's Government of Great Britain and Northern Ireland, United Kingdom

[21] Appl. No.: 411,280

[22] Filed: Mar. 27, 1995

Related U.S. Application Data

[62] Division of Ser. No. 307,686, filed as PCT/GB93/00604 Mar. 24, 1993.

[30] Foreign Application Priority Data

Mar. 26, 1992 [GB] United Kingdom ............... 9206645
Mar. 26, 1992 [WO] WIPO ........................ GB93/00604

[51] Int. Cl.⁶ .................................................. A61K 35/00
[52] U.S. Cl. .................................................... 424/115
[58] Field of Search .................................... 424/115

[56] References Cited

U.S. PATENT DOCUMENTS 4,663,162  5/1987  Kado et al. ........................ 424/92
4,764,371  8/1988  Pusey et al. ....................... 424/92

FOREIGN PATENT DOCUMENTS 0276132  7/1988  European Pat. Off. ..
0376775  7/1990  European Pat. Off. ..

*Primary Examiner*—Jerome D. Goldberg
*Attorney, Agent, or Firm*—Nixon & Vanderhye

[57] ABSTRACT

The present invention relates to novel bacterial isolates and to their use as agents, or source of agents, antagonistic to growth of rot causing organisms. Particularly the present invention provides novel isolates of bacteria of species *Pseudomonas fluorescens*, *Serratia liquefaciens*, *Serratia plymuthica*, *Bacillus subtilis*, *Bacillus pumilis* and *Bacillus polymyxa* which are particularly effective in inhibiting the growth of organisms of the post-harvest disease causing fungi *Botrytis cinerea* and *Alternaria brassicicola*. Further provided are antibiotics derived from the Bacillus species.

8 Claims, 23 Drawing Sheets

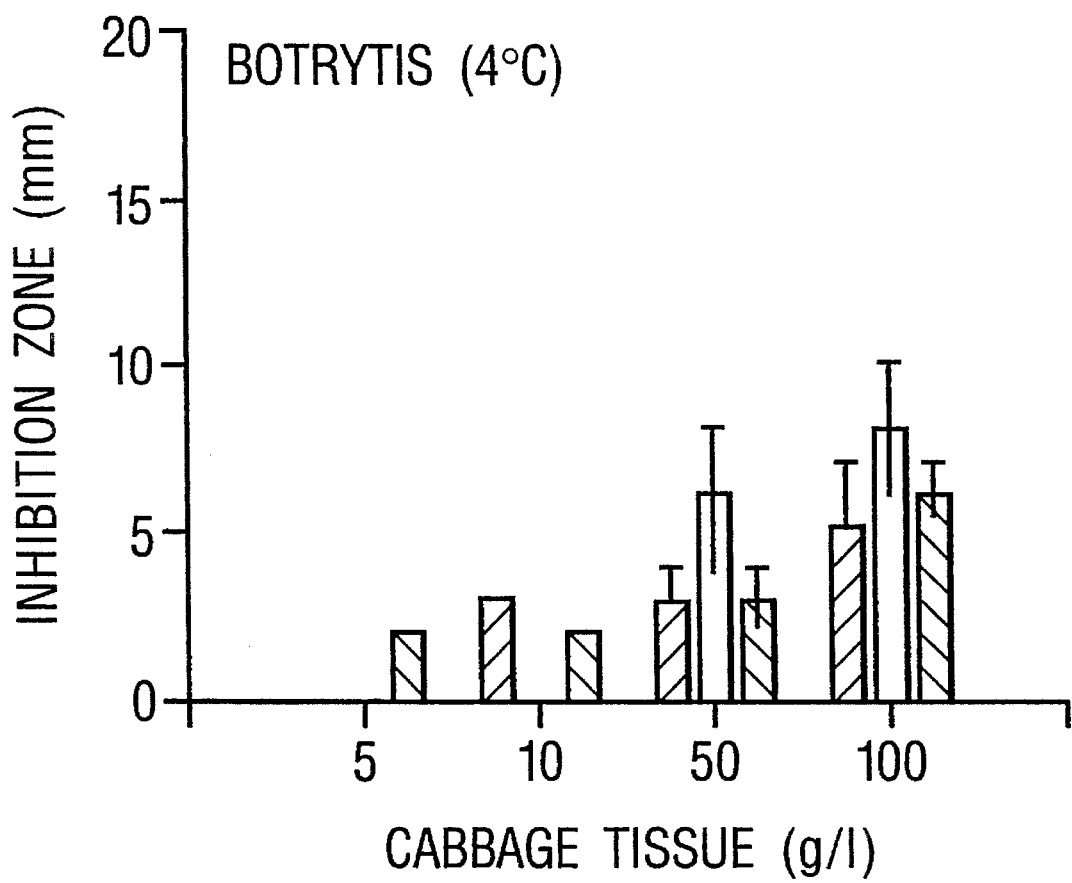

ically, the Pseudomonas and Serratia isolates of the
ANTIBIOTICS FOR BIOLOGICAL CONTROL OF POST HARVEST DISEASES This is a Division of application Ser. No. 08/307,686, filed as PCT/GB93/00604 Mar. 24, 1993 now abandoned.

The present invention relates to novel bacterial isolates and to their use as agents, or source of agents, antagonistic to growth of rot causing organisms. Particularly the present invention provides novel isolates of bacteria of species *Pseudomonas fluorescens*, *Serratia liquefaciens*, *Serratia plymuthica*, *Bacillus subtilis*, *Bacillus pumilis* and *Bacillus polymyxa* which are particularly effective in inhibiting the growth of organisms of the post-harvest disease causing fungi *Botrytis cinerea* and *Alternaria brassicicola*. Further provided are antibiotics derived from the Bacillus species.

Post-harvest losses during storage of plant produce are caused, inter alia, by water loss, leaf senescence, regrowth and rotting, the latter particularly caused by fungal and bacterial pathogens. Such post-harvest losses can be greatly reduced by storage at low temperatures (eg. 1°–20° C.) and high relative humidity (eg. 95%) (Robinson et al. 1975). Under these storage conditions *B. cinerea* is the prevalent fungus found on stored cabbages and the main reason for losses (Geeson 1978, Brown et al. 1975); it being an opportunistic pathogen of a wide range of leafy vegetables attacking weakened, wounded or senescent leaf tissues and is also known to attack various fruit (see U.S. Pat. No. 5,041,384). Healthy leaf tissues have, however, been described as being highly resistant to Botrytis attack (Newhook 1951). Initial resistance of the exposed outer leaves is also likely to be the reason for the finding that Botrytis rot of cabbages usually starts after 2–3 months of cold storage and is often confined to the outer, dried out, senescent cabbage leaves (Wale 1980).

To prevent fungal spoilage it is common practice in many countries to spray cabbages with systemic fungicides in the field and to dip harvested cabbage heads in fungicide solutions prior to storage (Brown et al. 1975). Since the oncogenic nature of many of the most commonly used fungicides is increasingly recognized and because the persistence of most fungicides is increased by the low storage temperatures the postharvest use of fungicides is of growing concern.

Additionally, resistance to the fungicides used has been reported (Spotts & Cervantes 1986) and suppression of the main spoilage organism *B. cinerea* by fungicides such as benomyl has been shown to result in increased population of *A. brassicicola* which causes a more penetrating rot of cabbage heads than *B. cinerea* (Wale & Epton 1979).

Control of post-harvest fungal pathogens by bacteria and yeast antagonists such as *Bacillus subtilis*, *Pseudomonas cepacia*, *Pseudomonas syringae*, *Enterobacter aerogenes*, *Enterobacter cloacae* and *Debaryomyces hansenii* has been described for a variety of stored vegetables and fruit including apple, apricot, cherry, citrus, grape, nectarine, peach, pear, pepper, persimmon, plum, potato and tomato (see Wilson & Wisniewski, 1989, for a recent review). However, the majority of studies have only investigated the antagonistic effects at temperatures of around 20° C., but not at temperatures of between 1° and 10° C. which are used for commercial storage of most fruit and vegetables. Additionally very few publications have tested the persistence of antagonists on plant surfaces or compared microbial populations on stored plant organs with the antagonistic microflora.

The present invention provides novel bacterial isolates of species which have the property of inhibiting the growth of fungal species on post-harvest products; these being species of Pseudomonas, Serratia and Bacillus. Most advantageously, the Pseudomonas and Serratia isolates of the present invention have the property of being able to inhibit fungal growth at cold storage temperatures, eg. below 10° C., typically from 0° to 4° C. Furthermore, the Bacillus isolates have the property of expressing an antibiotically active fraction also provided by the invention which itself is capable of isolation in pure or semipure form and being used to inhibit growth of such fungal species.

It should be realised that the isolates of the present invention have been selected from a background population of many thousands of such strains which are not effective. However, given access to the deposited isolates referred to above, and the data and protocols relating thereto below, it will be recognised by those skilled in the art that further related strains with similar antagonistic qualities will be isolatable and thus the scope of the present invention covers such related strains in so far as then might be recognised by comparison with the strains provided and the data and protocols herein.

Samples of the novel bacterial isolates of the present invention have been deposited under the terms of the Budapest Treaty on the International Recognition of the Deposit of Microorganisms for the purpose of patent procedures at the UK National Collection of Industrial and Marine Bacteria, 23 St Machar Drive, Aberdeen, AB2 1RY, UK, under the following accession numbers:

| Designation | | Accession No. | Date of Deposit. |
| --- | --- | --- | --- |
| *Pseudomonas fluorescens* | CL42 | NCIMB 40495 | 24.03.92 |
| *Pseudomonas fluorescens* | CL66 | NCIMB 40490 | 23.03.92 |
| *Pseudomonas fluorescens* | CL82 | NCIMB 40497 | 31.03.97 |
| *Serratia plymuthica* | CL43 | NCIMB 40493 | 23.03.92 |
| *Serratia liquefaciens* | CL80 | NCIMB 40492 | 23.03.92 |
| *Bacillus subtilis* | CL27 | NCIMB 40491 | 23.03.92 |
| *Bacillus pumulis* | CL45 | NCIMB 40489 | 23.03.92 |

The present invention provides isolated bacteria having the identifying characteristics of an isolate selected from the group consisting of NCIMB 40489, NCIMB 40490, NCIMB 40491, NCIMB 40492, NCIMB 40493, NCIMB 40494, NCIMB 40495 and NCIMB 40497. Such isolates share the characteristic of inhibiting growth of fungi of species *A. brassicicola* and/or *B. cinerea* on cabbage tissue:agar:water mixtures.

A particularly preferred aspect of the present invention provides a bacterial isolate having the identifying characteristics of an isolate selected from the group consisting of NCIMB 40490, NCIMB 40492, NCIMB 40493, NCIMB 40495 and NCIMB 40497, said isolate being capable of inhibiting growth of *A. brassicicola* and/or *B. cinerea* on cabbage leaves at temperatures of 20° C. or less, more preferably at 10° C. or less, most preferably at 4° C. or less. More preferably the isolate is of species selected from the group consisting of *Pseudomonas fluorescens*, *Serratia plymuthica* and *Serratia liquefaciens*.

A further preferred aspect of the present invention provides a bacterial isolate having the identifying characteristics of an isolate selected from the group comprising NCIMB 40489 and NCIMB 40491, said isolate being capable of inhibiting growth of *A. brassicicola* and/or *B. cineria* on cabbage leaves at temperatures of about 20° C.

More preferably the isolate is capable of production of an antibiotic fraction when cultured upon a broth of homogenised cabbage leaves of concentration 50 g or more per liter of water, said antibiotic being capable of inhibiting growth of said *A. brassicicola* and/or *B. cineria* on cabbage leaves at temperatures of about 20° C.

A further aspect of the invention provides aqueous suspensions of bacteria of one or more of the bacterial isolates of the invention, preferred suspensions being of sufficient cfu/ml to inhibit the fungal growth referred to above on fruit and/or vegetables that have been dipped therein, and further to biologically pure cultures of such bacteria at higher cfu/ml for preparing suspensions for such dipping.

The present invention thus further provides a process for the prevention of fungal disease in post-harvest vegetables and/or fruit products comprising dipping said products into suspension of bacteria as described above. Preferably the suspension will contain from between $10^4$ and $10^9$, more preferably between $10^5$ and $10^8$ cfu/ml. Using the non-Bacillus group cold storage is a preferred option.

A still further aspect of the invention provides antibiotics obtainable by culturing isolated bacteria of the type of NCIMB 40489 and/or NCIMB 40491 in a medium comprising homogenised cabbage leaves and water in a ratio of 5 g to 100 g/liter. Further provided are compositions characterised in that they have such antibiotics as active ingredients.

The isolates, their efficacy against fungal growth, methods of selecting similar such isolates and methods for their use in achieving this in industrial application will now be exemplified, by way of illustration only by referral to the following Figures and Examples.

BRIEF DESCRIPTION OF THE FIGURES

FIG. 1. Inhibition zone diameter (mm) around bacterial colonies on cabbage agar containing different concentrations of cabbage tissue seeded with *A. brassicicola* and *B. cinerea*. ■=CL42; ■=CL66; □=CL82.

FIG. 2. Mean inhibition zone diameter (mm) (vertical bars=standard deviation) around bacterial colonies on cabbage agar containing different concentrations of cabbage tissue seeded with *A. brassicicola* and *B. cinerea* (mean of 3 determinations per isolate). ■=*Serratia plymuthica* (CL43); □=*Serratia liquefaciens* CL57: isolates 58, 59, 61, 62 and 80 showed similar results.

FIG. 3. *Bacillus subtilis* isolate CL27 growth, sporulation and production of antagonistic activity against *A. brassicicola* and *B. cinerea* in cabbage broth (A: CB5, B: CB10) batch culture. Antifungal activity was assayed in Sens-acute plates containing fungal seeded CA5. ■=cfu; ○=spores; ■=activity against *B. cinerea;* □=activity against *A. brassicicola.*

FIG. 4. *Bacillus pumilus* isolates CL45 growth, sporulation and production of antagonistic activity against *A. brassicicola* and *B. cinerea* in cabbage broth (A: CB5, B: CB10) batch culture. Antifungal activity was assayed in Sens-acute plates containing fungal seeded CA5. ●=cfu; ○=spores; ■=activity against *B. cinerea;* □=activity against *A. brassicicola.*

FIG. 5. *Bacillus subtilis* isolate CL27 growth, sporulation and production of antagonistic activity against *A. brassicicola* and *B. cinerea* in nutrient broth (A: NB, B: NB+Mg, C: NB+1% glucose) batch culture. Antifungal activity was assayed in Sens-acute plates containing fungal seeded CA5. ●=cfu; ○=spores; ■=activity against *B. cinerea;* □=activity against *A. brassicicola.*

FIG. 6. *Bacillus pumilis* isolate CL45 growth, sporulation and production of activity against *A. brassicicola* and *B. cinerea* in nutrient broth (A: NB, B: NB+Mg) batch culture. Antifungal activity was assayed in Sens-acute plates containing fungal seeded CA5. ●=cfu; ○=spores, ■=activity against *B. cinerea;* □=activity against *A. brassicicola.*

FIG. 7. *Bacillus subtilis* isolate CL27 growth, sporulation and production of activity against *A. brassicicola* and *B. cinerea* in defined medium (A: DM, B: DM+1% glucose) batch culture. Antifungal activity assayed in Sens-acute plates containing fungal seeded CA5. ●=cfu; ○=spores; ■=activity against *B. cinerea;* □=activity against *A. brassicicola.*

FIG. 8. Effect of medium pH on the activity of antibiotics from Bacillus isolate CL27 and CL45 batch cultured extracted 2 days (A&C) or 4 days (B&D) after inoculation. In A, B, and D inhibition of the pathogen was determined on Sens-acute Micro-detection plates containing *B. cinerea* seeded CA5 medium, in C on PDA. Batch culture media: ●=CB10; ○=CB5; ■=NB; □=NB+Mg.

FIG. 9. Effect of nutrient type and concentration in the assay medium (homogenized cabbage tissue or potato dextrose broth solidified with 10 g/l agar) on the size of inhibition zones formed. Media was seeded with *B. cinerea* spores. The crude extract used was taken after 3 days from *B. subtilis* isolate CL27 CB5 batch cultures. Different concentrations of antibiotics were obtained by diluting the crude extract (conc. 100%) with sterile CB5. Assay media used: Δ=50 mg/ml; ○=100 mg/ml; □=200 mg/ml homogenized cabbage tissue; ▲=¼ strength PDB; ●=½ strength PDB ; ■=full strength PDB (Potato dextrose broth).

EXAMPLE 1

Isolation of Antagonist Strains from Brassica Leaf Tissues

A 10×10 cm square was aseptically cut from the outermost cabbage leaf of a head and placed in a plastic bag with 25 ml of sterile Ringer's solution. The tissue was then placed in a stomacher for 10 min to remove surface organisms. Appropriate dilution steps were plated onto nutrient agar, cabbage agar (homogenized cabbage leaf tissue either 10 g [CA1], 20 g [CA2], 50 g [CA5] or 100 g [CA10]) and 10 g agar per liter water), cabbage agar seeded with Botrytis spores (as described below), Sabourough agar (Oxoid) and potato dextrose agar (Oxoid). Antagonistis were detected by the inhibition zones formed either when leaf washings were directly plated on Botrytis-seeded agar or after replica-plating of colonies onto Botrytis-seeded agar.

Identification of the General Microflora on Cabbage Leaves

The number of colonies of filamentous fungi was counted directly on isolation plates. To estimate the number of yeasts, fluorescent pseudomonads and Enterobacteriaceae, 140 colonies were randomly picked from isolation plates and identified. Phase contrast microscopy was used to identify yeasts and to examine bacteria for motility. Since all bacteria found were Gram-negative the isolates showing motility and fluorescence on King's medium B were classified as fluorescent pseudomonads and those showing anaerobic growth (Hugh & Leifson 1953) as Enterobacteriaceae. Other bacterial isolates were not identified.

The number of Bacillus spores was estimated from the number of colonies developing after 20 fold concentration of the leaf washings by centrifugation at 3600 rev/min and heating (800° C. for 20 min).

Identification of Bacterial Antagonists

Gram's stain (Jensen's modification), shape, motility (under phase contrast microscopy), oxidase test (Kovacs 1956), heating (20 min at 80° C.) and the oxidation/fermentation test (Hugh & Leifson 1953) were used for initial identification. Oxidase-negative, acidifying Gram-negative rods (Enterobacteriaceae) were further tested with API 20E, oxidase-positive, non-acidifying Gram-negative rods with API 20NE and heat resistant Gram-positive rods (Bacillus spp.) with API 20E and 50CHB test strips (API-BioMerieux, UK.). Results were analysed by the API computer identification software and identification of *Serratia liquefaciens* (Grimes & Hennerty) was confirmed by testing acid production from raffinose, manolate, lactose and adonitol using the methods described by Brenner (1984).

Preparation of Fungal Inoculum

All fungal stock cultures were grown on cabbage agar 5 (CA5; 50 g homogenized cabbage tissue, 10 g agar, 1 liter distilled water) at 4° C. in the dark. Malt extract agar (MA) was used for spore production. *Botrytis cinerea* was grown for 5 days at 20° C. in the dark followed by 3 days under UV-light to induce sporulation and *Alternaria brassicicola* was grown for 14 days at 20° C. prior to use in experiments. Spores were harvested by pouring 10 ml of sterile Ringer's solution onto a fungal plate and suspending spores using a bacteriological loop. Spore suspensions were filtered through a double layer of muslin and adjusted to a concentration of $4 \times 10^6$ spores/ml using a haemacytometer.

Preparation of Bacterial Inoculum

Inocula were prepared by suspending bacterial growth from a 24 hr NA culture in ¼ strength Ringer's solution. The turbidity was then adjusted to an absorbance of 1.0 at 625 nm using a ULTRO SPEC 4051 spectrophotometer (LKB BIOCHROM Ltd., Cambridge, UK.) giving a bacterial concentration of $7 \times 10^8$ cfu/ml for *Pseudomonas fluorescens* and $5 \times 10^8$ cfu/ml for Serratia isolates (the number of cfu was obtained by plating dilution steps of the suspension onto NA). Lower inoculum levels were prepared by appropriate dilution in ¼ strength Ringer's solution.

'In vitro' Assay for Antifungal Activity

Twenty ml of liquid CA5 was cooled to 40° C. (*Botrytis cinerea* spores are very sensitive to heating) and inoculated with 0.2 ml of a fungal suspension containing $4 \times 10^5$ spores/ml. After the agar had set plates were dried in a laminar flow cabinet for 90 min and then inoculated immediately with a loopful of a bacterial suspension containing $2 \times 10^8$ cfu/m. When testing the antibiotic activity in crude extracts (cell free culture filtrates) from batch cultures of Bacillus spp. fungal seeded medium was poured into sens-acute Micro detection trays (Intl. Patent Application No PCT/GB90/01067; Proteus Molecular Design Ltd., Marple, Cheshire, UK); After the agar had set 4 mm wells were cut into the agar and filled with 30 µl of the crude extract. Inhibition zone diameters around colonies or wells were measured 2 days after inoculation of bacteria or cell free extracts of Botrytis and 4 days after inoculation of Alternaria seeded media.

'In vivo' (Leaf Disk) Assay for Antifungal Activity

Leaf disks (15 mm diameter) were cut from internal leaves of cabbages (the outermost 5 leaves were discarded) using a corkborer. Disks were transferred to a 25 ml universal bottle and heated for 20 min at 50° C. This treatment was found necessary to break the natural resistance of non-senescent internal cabbage leaf tissue to enable infection by *B. cinerea* and *A. brassicicola* spores. Disks were left to cool and then suspended in a bacterial suspension containing $7 \times 10^8$, $7 \times 10^7$ or $7 \times 10^6$ cfu/ml for *P. fluorescens* isolates and $5 \times 10^8$, $5 \times 10^7$ or $5 \times 10^6$ cfu/ml for Serratia isolates. This resulted in approximately $10^7$, $10^6$ or $10^5$ cfu/disk, when the number of cfu on leaf disks was determined immediately after inoculation. This determination was carried out by washing (10 min at speed 6 using a Gallenkamp wrist shaker) disks in 2 ml sterile ¼ strength Ringer's solution to remove bacteria from the plant surfaces and plating at appropriate dilutions on nutrient agar.

After inoculation with bacteria disks were transferred to a tissue culture assay plate (8.5×13 cm) with 24 wells of 15 mm diameter. A non-heated disc was placed under the inoculated heated disk to mimic the situation in a stored cabbage head where susceptible, senescent outer leaves overlay resistant metabolically active inner leaves. Assay plates were then placed open in a laminar flow cabinet until the disk surfaces were dry. Afterwards 2.5 µl of fungal suspension containing $10^3$, $10^4$ or $10^5$ spores was placed in the centre of the disk. Assay plates were placed over water in a seed tray (15×20 cm) and the tray sealed with plastic film. The humidity in trays was measured using a Vaisala 100 humidity probe (Vaisala OY, PL26, Helsinki, Finland) and found to be between 97 and 99% throughout the experiment. Trays were inoculated at 40° C. in darkness for 10 weeks.

Persistence of Reinoculated Antagonistis on Leaf Surfaces

To determine the persistence of reinoculated antagonistic bacteria on leaf surfaces, non-heated leaf disks (1.5 cm diameter) were dipped in a bacterial suspension and incubated in assay plates as described above. Prior to the removal of surface microorganisms a 1×1 cm square was cut from the disk in order to avoid sampling bacteria on the cut edges of the disk. The square was suspended in 2 ml of Ringer's solution and shaken for 10 min using a Gallenkamp wrist shaker at speed 6 to remove surface bacteria. The number of antagonistic bacteria in the leaf washing was determined on the basis of their in vitro antagonism against *A. brassicicola* by plating leaf washings on CA5 seeded with *A. brassicicola* and counting of colonies with inhibition zones.

General and Antagonistic Microflora Found on Brassica spp.

When the number of viable microorganisms on the cabbage leaf surface was determined, leaves were found to harbour approximately $10^3$–$10^4$ cfu/cm$^2$ (Table 1). Of these between 1 and 15% were yeasts, 65–80% were fluorescent pseudomonads, 5–20% Enterobacteriaceae. Less than 1% of surface microorganisms were filamentous fungi and Bacillus spp. could only be isolated by the selective enrichment procedure described above. The number of viable Bacillus spores was between 1 and 20 cfu/20 cm$^2$. Numbers of surface microorganisms were lower on internal leaves of cabbages Table 6 shows the numbers found on the 6th leaf.

TABLE 1

Numbers of viable microorganisms (cfu)/cm² on Dutch White and January Glory cabbage leaves.

| Isolation medium | Dutch White | | | January Glory | | |
|---|---|---|---|---|---|---|
| | n | mean | STD | n | means | STD |
| CA5 | 4 | $1 \times 10^4$ | $5 \times 10^3$ | 5 | $6 \times 10^3$ | $2 \times 10^3$ |
| NA | 7 | $8 \times 10^3$ | $3 \times 10^3$ | 4 | $5 \times 10^3$ | $2 \times 10^3$ |
| SA | 7 | $5 \times 10^3$ | $2 \times 10^3$ | 4 | $4 \times 10^3$ | $5 \times 10^3$ | n = number of leaves examined
STD = standard deviation

Sixty one percent of antagonistic bacterial strains isolated from Brassica spp. were oxidase positive fluorescent pseudomonads, 30% were Bacillus and 9% were Serratia species. The different groups are described in separate sections below.

EXAMPLE 2

Pseudomonas fluorescens: General Characteristics

Fluorescent pseudomonads appears to be a major part of the natural flora of cabbage leaves since they were repeatedly isolated in large numbers. All antagonistic fluorescent pseudomonads isolated belonged to the species *Pseudomonas fluorescens*. All strains were isolated from conventionally and organically grown 'Dutch White' or 'January Glory' cabbages, broccoli or Brussels sprouts using a variety of different isolation media (Table 2). There were two main groups of antagonistic pseudomonads, those producing fluorescent pigments on nutrient agar (group 1: CL6,7,9,10,11, 12,15,16,18,21,29,39,40) and those which did not (group 2: CL42,66,74,82,13,14,17,22,23,30,31–37,39).

In vitro Inhibition

Group 1 pseudomonads produced small zones of inhibition (<4 mm) on *B. cinerea* and *A. brassicicola* seeded CA5 agar, while Group 2 included: a. strains CL31–CL37 and CL49 which caused rotting of cabbage leaves (not tested further for 'in vitro' antagonism) and b. all strains (CL42, 49, 66, 74, 82 and 90) which produced large inhibition zones (Table 2). Inhibition zones formed by different strains of group 1 pseudomonads at different temperatures and nutrient concentrations in the medium were generally small (1–4 mm, individual results not shown). However, when inhibition zones of strains from group 2 were compared, strain specific patterns were found (Table 2). The size of inhibition zones on cabbage agar decreased with decreasing concentrations of nutrients in the medium (between 5 and 100 g/l of cabbage tissue) for deposited strains CL42 and CL82. However, strain CL66 showed increasing zones of inhibition with decreasing concentration of nutrients on cabbage agar seeded with Alternaria but decreasing zones of inhibition in Botrytis seeded cabbage agar. Significantly the inhibition zones at 4° C. were larger at all nutrient concentrations with both fungi around CL82 colonies and around CL42 colonies on Alternaria seeded agar than at 10° C.

TABLE 2

In vitro inhibition of *Alternaria brassicicola* and *Botrytis cinerea* by non-pathogenic group 2 Pseudomonas spp. isolated from Brassica spp. on CA5 (means from 3 determinations)

| | | | Inhibition zone diameter (mm) | | | | | |
|---|---|---|---|---|---|---|---|---|
| | | | Alternaria | | | Botrytis | | |
| code | Isolate Origin | Isolation medium | 20° C. | 10° C. | 4° C. | 20° C. | 10° C. | 4° C. |
| CL42 | DWL | NA | 8 | 8 | 12 | 12 | 13 | 13 |
| CL49 | DWL | CA5 | 4 | 6 | 9 | 4 | 2 | 13 |
| CL66 | JGL | CA5 | 8 | 8 | 13 | 8 | 8 | 6 |
| CL74 | DWLo | NA | | | 5 | | | 5 |
| CL82 | DWL | CA5 | 6 | 7 | 9 | 6 | 6 | 3 |
| CL90 | JGL | CA5 | | | 3 | 4 | | 4 |

DWL Dutch white cabbage leaves
DWLo Dutch white cabbage leaves (organically grown)
JGL January Glory cabbage leaves

In vivo Inhibition

Pseudomonas antagonists also suppressed infection and disease development on cabbage tissue when cabbage leaf disk assay was used to detect 'in vivo' antagonism. *P. fluorescens* isolates CL42, CL66 and CL82 showed best control of both fungi on cabbage disks—preventing development of disease symptoms on disks when dipped in a suspension of $7 \times 10^6$ cfu/ml; CL73 only gave intermediate control.

TABLE 3

Suppression of *Botrytis cineria* and *Alternaria brassicicola* by Pseudomonas spp. on cabbage leaf disks (each experiment was x3)

| | | Botrytis cinerea inoculum No. of spores/disk | | | Alternaria brassicicola inoculum No. of spores/disk | | |
|---|---|---|---|---|---|---|---|
| Bacterial isolate | Bacteria inoculum (cfu/ml) | $10^4$ | $10^3$ | $10^2$ | $10^4$ | $10^3$ | $10^2$ |
| CL42, 66, 82 | $7 \times 10^8$ | + | 30 | + | + | + | + |
| | $7 \times 10^7$ | + | + | + | + | + | + |
| | $7 \times 10^6$ | V | + | + | + | + | + |

TABLE 3-continued

Suppression of *Botrytis cineria* and *Alternaria brassicicola* by
Pseudomonas spp. on cabbage leaf disks (each experiment was x3)

| Bacterial isolate | Bacteria inoculum (cfu/ml) | *Botrytis cinerea* inoculum No. of spores/disk | | | *Alternaria brassicicola* inoculum No. of spores/disk | | |
|---|---|---|---|---|---|---|---|
| | | $10^4$ | $10^3$ | $10^2$ | $10^4$ | $10^3$ | $10^2$ |

+ inhibition
− no inhibition of fungal growth
V variable results
ND not determined
End of experiment (6 weeks after control discs showed fungal growth)

EXAMPLE 3

Serratia spp.

General Characteristics

Nine percent of antagonistic bacterial strains isolated from Brassica spp. were Serratia spp. (Enterobacteriaceae), eight strains being *Serratia liquefaciens* and one strain being *Serratia plymuthica*. All strains were isolated from conventionally and organically grown 'Dutch White' or 'January Glory' cabbages using a variety of different isolation media (Table 4). No antagonistic Enterobacteriaceae could be isolated from Brussel's sprout or broccoli.

Serratia strains grew well and showed 'in vitro' antagonism in CA5 medium at temperatures of between 4° and 20° C. (Table 4). Inhibition zones on Botrytis seeded CA5 were larger at 20° and 10° C. but smaller at 4° C. than on Alternaria seeded CA5. It should be noted that Botrytis grew faster at all temperatures (developing visible growth on the medium) than Alternaria. Inhibition zones of *S. liquefaciens* strains CL57, 58, 59, 61, 62, 73 and 80 were found to have a similar size, but smaller than those of *S. plymuthica* strain CL43.

inhibition zones formed around CL43 colonies at 10° C. with 10 g/l of cabbage tissue which are larger (FIG. 2). Inhibition zones of *S. plymuthica* strain CL43, however, were generally larger and CL43 was the only strain exhibiting significant antagonism at low nutrient concentrations (5 and 10 g/l; FIG. 2).

TABLE 5

Suppression of *Botrytis cinerea* and *Alternaria brassicicola* by
Serratia spp. on cabbage leaf disks at 4° C. (each experimet x3)

| Bacterial isloate inoculum (cfu/ml) | | *Botrytis cinerea* inoculum No. of spores/disk | | | *Alternaria brassicicola* inoculum No. of spores/disk | | |
|---|---|---|---|---|---|---|---|
| | | $10^4$ | $10^3$ | $10^2$ | $10^4$ | $10^3$ | $10^2$ |
| *Serratia plymuthica* | | | | | | | |
| CL43 | $5 \times 10^8$ | + | + | + | + | + | + |
| | $5 \times 10^7$ | V | + | + | + | + | + |
| | $5 \times 10^6$ | − | − | ' | V | + | + |
| *Serratia liquefaciens* | | | | | | | |
| CL80 | $5 \times 10^8$ | + | + | + | + | + | + |
| | $5 \times 10^7$ | V | + | + | + | + | + |
| | $5 \times 10^6$ | − | V | + | + | + | + |

See Table 3 for key.
Experiment end at 6 weeks after control disks showed fungal growth

In vivo Inhibition

Serratia antagonists also suppressed infection and disease development on cabbage tissue when the cabbage leaf disk assay was used to detect 'in vivo' antagonism. When cabbage disks were dipped in a bacterial suspension with $2 \times 10^9$ (results not shown), $2 \times 10^8$, $2 \times 10^7$ or $2 \times 10^6$ cfu deterioration of the tissue and the development of visible growth of *Botrytis cinerea* was inhibited to different extents, depending on bacterial species used and the fungal inoculum applied (Table 5).

TABLE 4

In vitro inhibition of *Alternaria brassicicola* and *Botrytis cinerea* by Serratia spp. isolated from Brassica on CA5 (mean of 3).

| | | | Inhibition zone diameter (mm) | | | | | |
|---|---|---|---|---|---|---|---|---|
| | | | Alternaria | | | Botrytis | | |
| code | Isolate Origin | Isolation medium | 20° C. | 10° C. | 4° C. | 20° C. | 10° c. | 4° C. |
| *S. plymuthica* | | | | | | | | |
| CL43 | DWL | NA | 16 | 17 | 11 | 16 | 24 | 5 |
| *S. liquefaciens* | | | | | | | | |
| CL57 | DWL | CA5 | 8 | 14 | 8 | 12 | 18 | 1 |
| CL58 | DWL | CA5 | 10 | 12 | 8 | 12 | 18 | 1 |
| CL59 | DWL | CA5 | 9 | 14 | 5 | 13 | 18 | 1 |
| CL61 | JGL | SA | 10 | 14 | 5 | 14 | 12 | 0 |
| CL62 | JGL | SA | 8 | 14 | 6 | 16 | 10 | 0 |
| CL73 | DWLo | CA5 | | | | 6 | | |
| CL80 | DWLo | CA5 | 10 | 14 | 6 | 15 | 10 | |
| CL90 | DWL | PDA | | | | 6 | | |

See Table 2 for key

The size of inhibition zone of all *S. liquefaciens* strains were found to be similar at all nutrient concentrations (between 5 and 100 g/l of cabbage tissue), except for

Persistence of Pseudomonas and Serratia on Cabbage Leaves

When the persistence of reinoculated antagonists was studied *P. fluorescens* and *Serratia* spp. were able to persist in large numbers on cabbage leaf surfaces at low temperatures (Table 6).

Table 6. Persistence of antagonistic *Pseudomonas fluorescens* and *Serratia plymuthica* on cabbage leaf disks after inoculation of disks by dipping into a bacterial suspension containing $7 \times 10^7$ cfu/ml for Pseudomonas and $5 \times 10^7$ cfu/ml for Serratia (mean is of 2 determinations).

| | Total No. of cfu/cm$^2$: (% of cfu showing antagonism against *Alternaria brassicicola*) | | | |
|---|---|---|---|---|
| Days after inoculation | Non-inoculated control | *P. fluorescens* CL42 | CL82 | *S. plymuthica* CL43 |
| 0 | $7 \times 10^2$ (0) | $5 \times 10^4$ (>99%) | $4 \cdot 10^4$ (>99%) | $3 \times 10^4$ (>99%) |
| 14 | $7 \times 10^2$ (o) | $2 \times 10^4$ (>99%) | $9 \times 10^3$ (98%) | $5 \times 10^4$ (>99%) |
| 28 | $1 \times 10^3$ (0.2*) | $4 \times 10^3$ (97%) | $6 \times 10^3$ (95%) | $2 \times 10^4$ (>99%) |
| 48 | $3 \times 10^3$ (0) | $5 \times 10^3$ (97%) | $2 \times 10^3$ (80%) | $2 \times 10^4$ (>99%) |

*one antagonistic colony was observed

EXAMPLE 4

Bacillus spp. General Characteristics

Thirty percent of all bacteria showing antagonism against *Botrytis cinerea* were found to be Bacillus spp. Fourteen Bacillus isolates were identified and found to be *B. subtilis* (8 isolates), *B. pumilus* (3 isolates) or *B. polymyxa* (3 isolates).

Antibiotic Production in vitro (Semiquantitative)

Bacillus isolates isolated from Brassica spp. did not grow at 4° and 10° C. (except for Bacillus strains CL47, 52, 64 and 67 which produced very poor growth after 4 weeks at 10 and 6 weeks at 4° C.). At 20° C. most strains produced large inhibition zones on CA5 medium (Table 7). However, Bacillus did not grow or failed to produce large inhibition zones at lower nutrient concentrations in the medium (Table 7).

EXAMPLE 5

Antibiotic Production in Batch Culture of Bacillus spp.

Cabbage broth (50 g [CB5] or 100 g [CB10] or homogenized cabbage leaves, 1 liter distilled $H_2O$), nutrient broth (NB: Oxoid), nutrient broth+0.005 g/l $MgSO_4$ (NB+Mg), nutrient broth+1% glucose (NB+1% glucose), a defined medium (DM: 2 g NH4Cl, 6 g $Na_2HPO_4$, 3 g $KH_2PO_4$ 3 g NaCl, 0.05 g $MgSO_4$ 7 $H_2O$, 5 mg L-methionine, 10 mg glycine, 2.5 mg L-aspartic acid, 10 g agar, 1 liter distilled $H_2O$) and DM+1% glucose were used as growth media. 100 ml of medium was transferred to 250 ml Erlenmeyer conical flasks and autoclaved and inoculated with bacteria from a 3 day old nutrient agar culture of the Bacillus strains. Amino acids were filter sterilised and added to the medium after autoclaving. Four ml of medium was sampled aseptically at various times after inoculation. The number of cfu was determined by plating of dilution steps (¼ strength Ringer's solution) of the sampled medium on nutrient agar. The number of Bacillus spores was determined by mixing 0.1 ml of absolute alcohol with 0.1 ml of the culture medium in wells of a microwell plates (0.3 ml wells; Nunc Ltd., DK) for 20 min (to kill off vegetative cells) before plating of dilution steps on nutrient agar.

Crude antibiotic extracts from the various media were made by centrifuging the liquid for 30 min at 3000 g using a Mistral 3000i centrifuge (Fisons, UK.). The supernatant was filtered through a 0.2 µm cellulose nitrate filter (Sartorius, Gottingen, Germany) to obtain cell free filtrates. To obtain lower concentrations of antibiotics, these crude extracts were then diluted with cabbage broth. 30 µl of the crude extract or the different dilutions were placed in 4 mm diameter wells in CA5 plates seeded with *B. cinerea* or *A. brassicicola*. When the effect of pH on the activity of antibiotics in crude extracts was determined the pH of the assay medium was adjusted to values of between 3 and 9 with HCl and NaOH prior to placing the crude extracts into the wells.

Antibiotic Production in vitro (Quantitative)

Inhibition zones were also formed around cell free culture filtrates of Bacillus spp. grown for 5 days in cabbage broth (CB5) or nutrient broth (NB) as growth media (Table 8). Cell free cabbage agar filtrates of Bacillus isolate CL27 and CL41 batch cultures had a very high activity against *Botrytis cinerea* and lower activity against *Alternaria brassicicola* (Table 8). Nutrient broth filtrates only had activity against *A. brassicicola* when Petri dishes were used to perform assays, but showed similar activity against *B. cinerea* and *A. brassicicola* when assays were performed in the more sensitive Sens-acute Microdetection plates; see Hampson et al.

Hampson et al 1992a gives a detailed description of the differences between Sensacute Micro-detection plates and Petri-dishes. Nutrient broth and cabbage broth (NB5) filtrates from strain CL45 were only active against *B. cinerea* (Table 8).

EXAMPLE 6

Effect of Culture Media

Figure 3A:
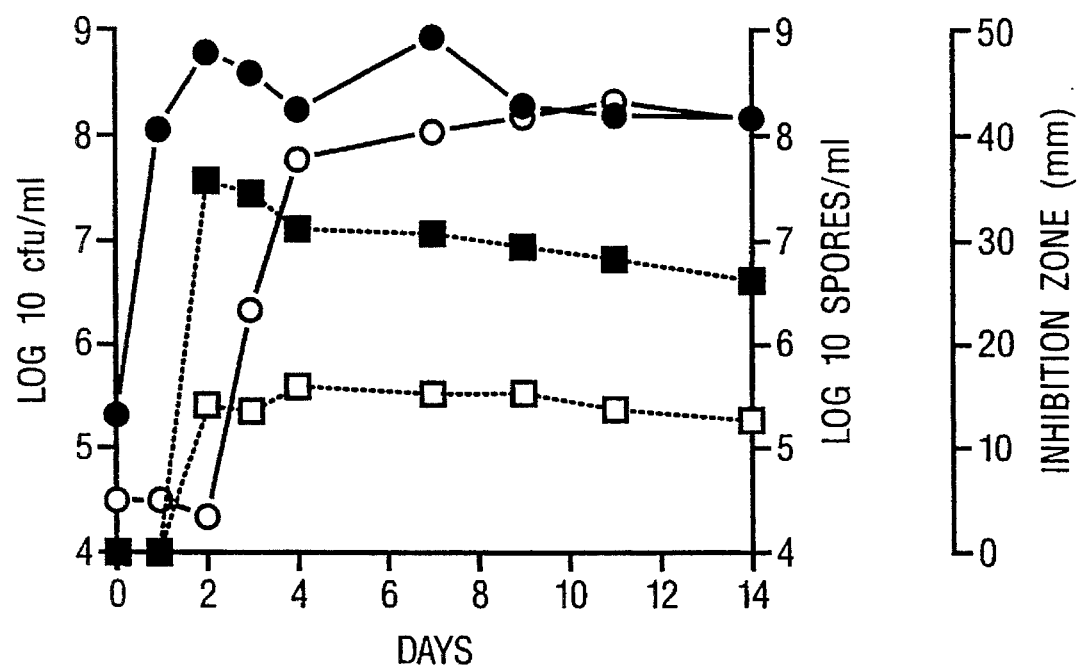
Figure 3B:
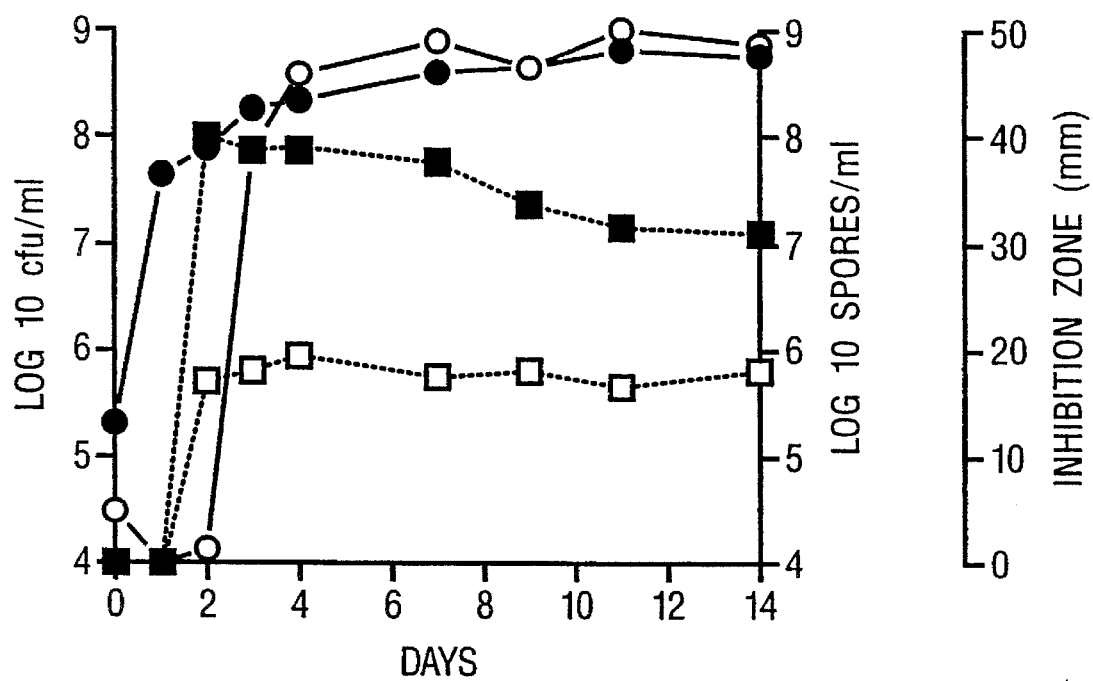
Figure 4A:
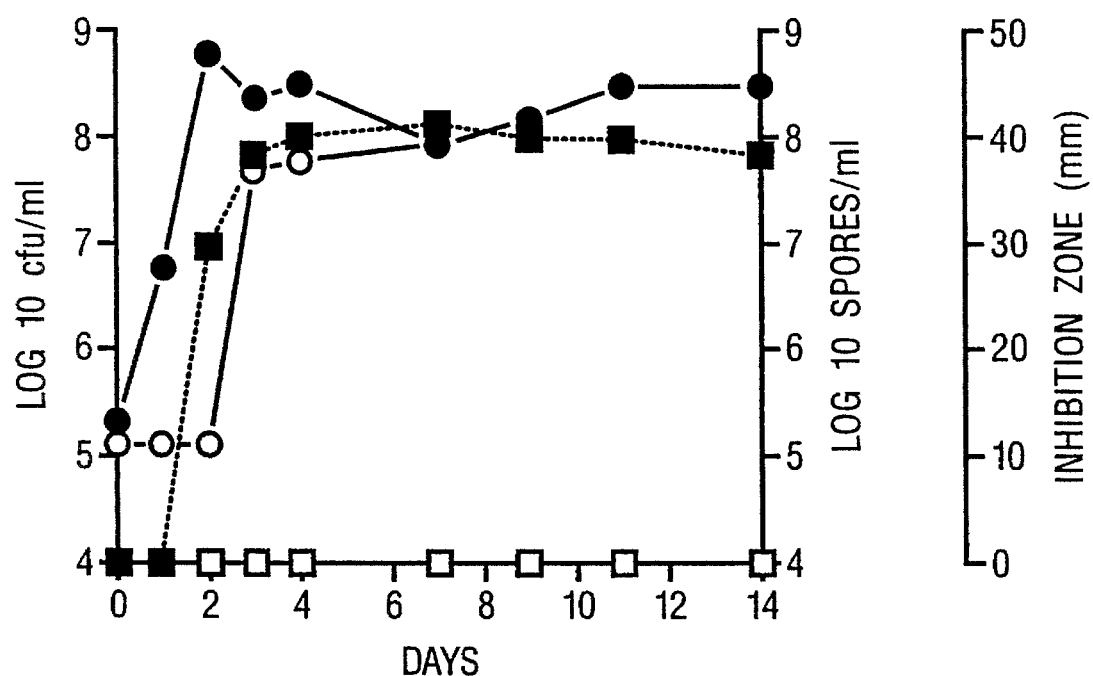
Figure 4B:
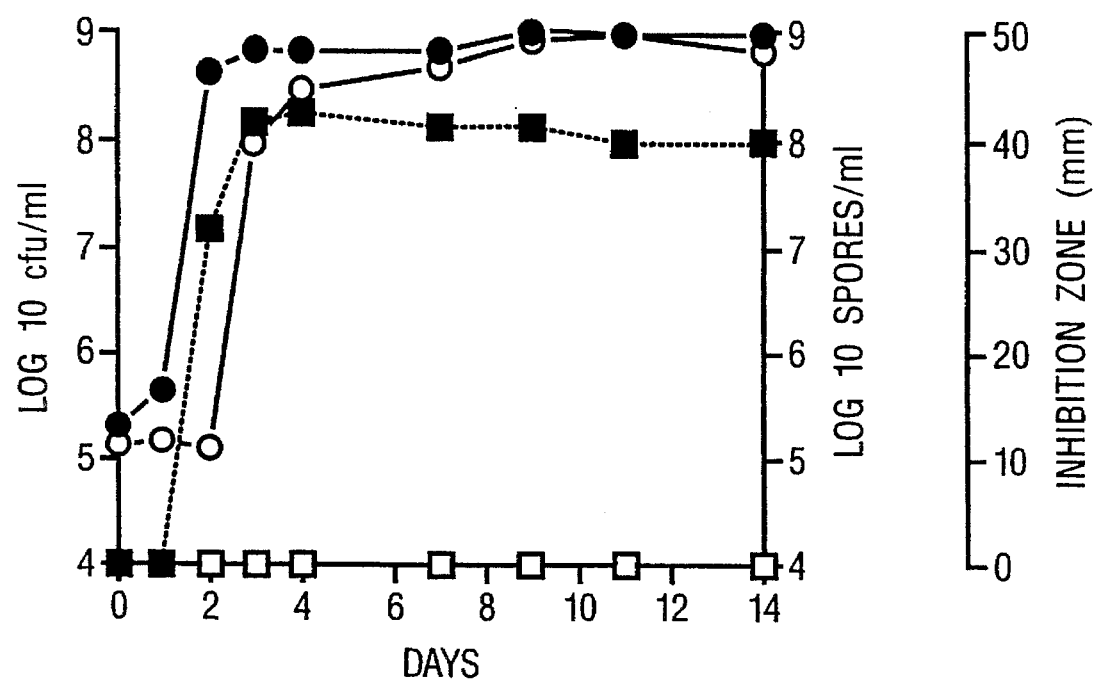
Figure 5A:
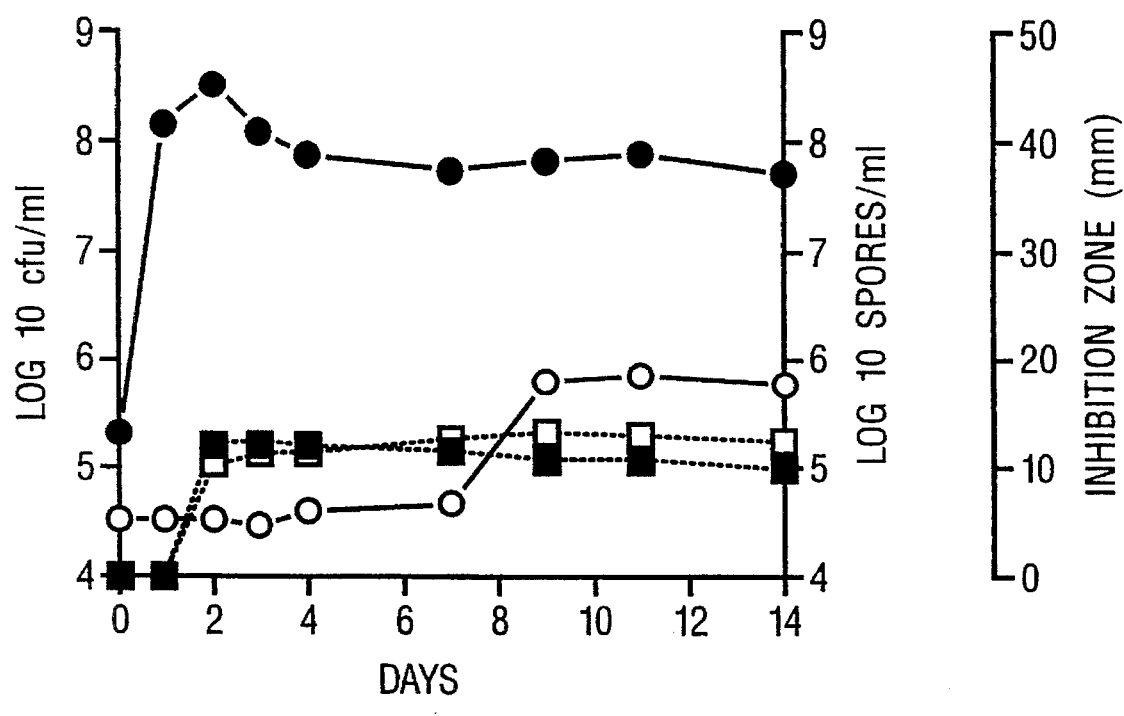
Figure 5B:
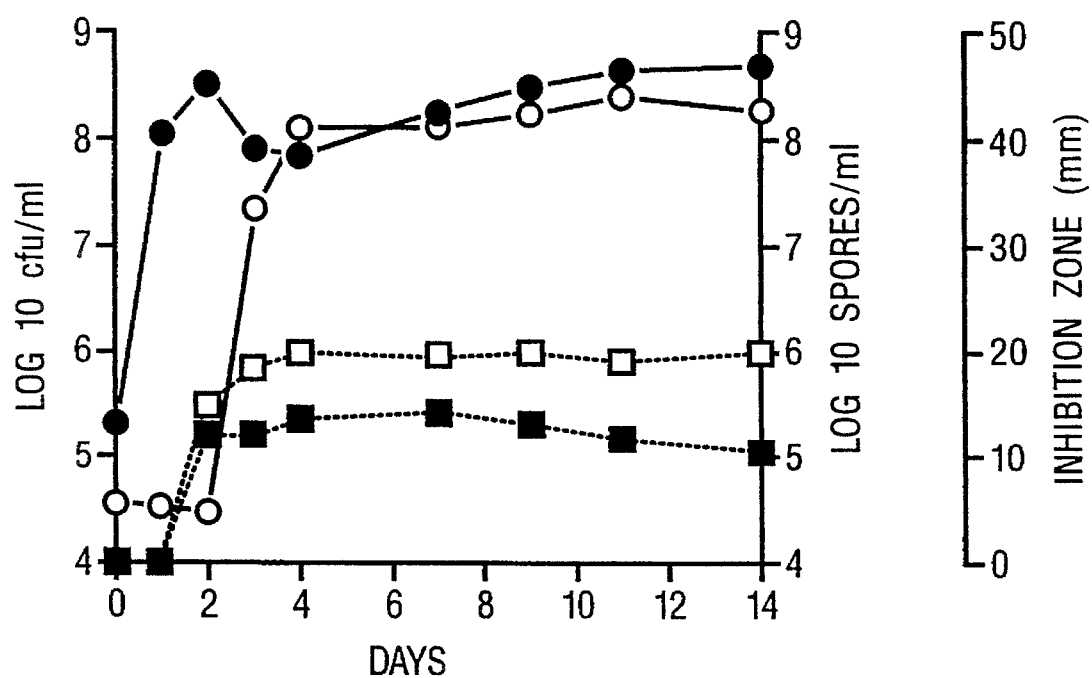
Figure 6A:
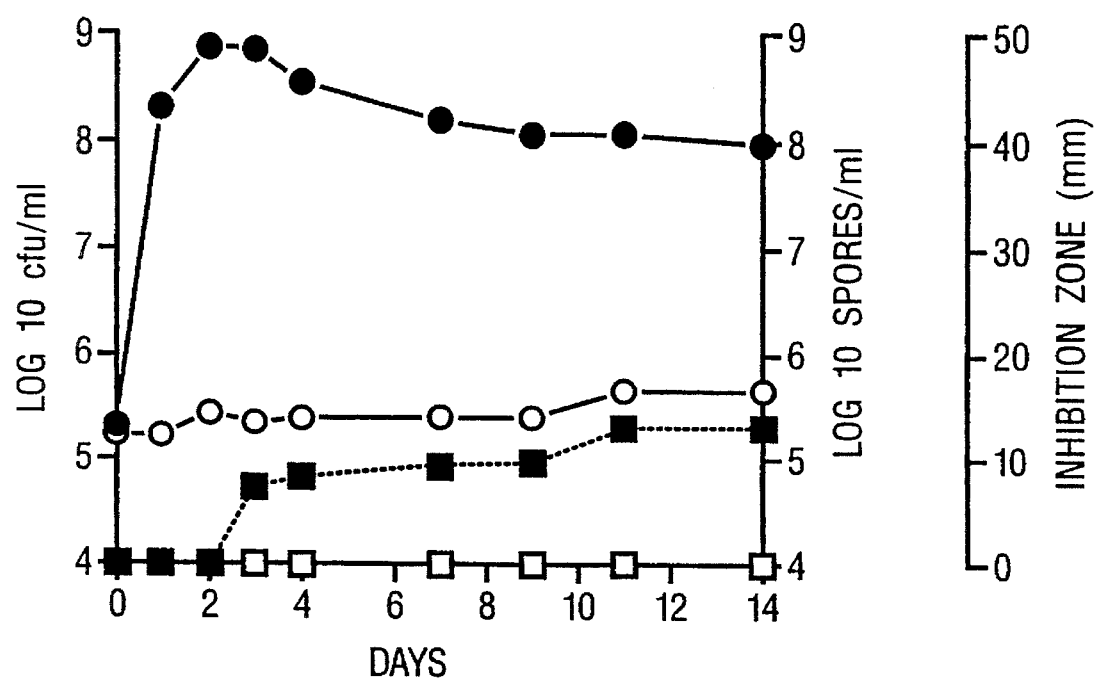
Figure 6B:
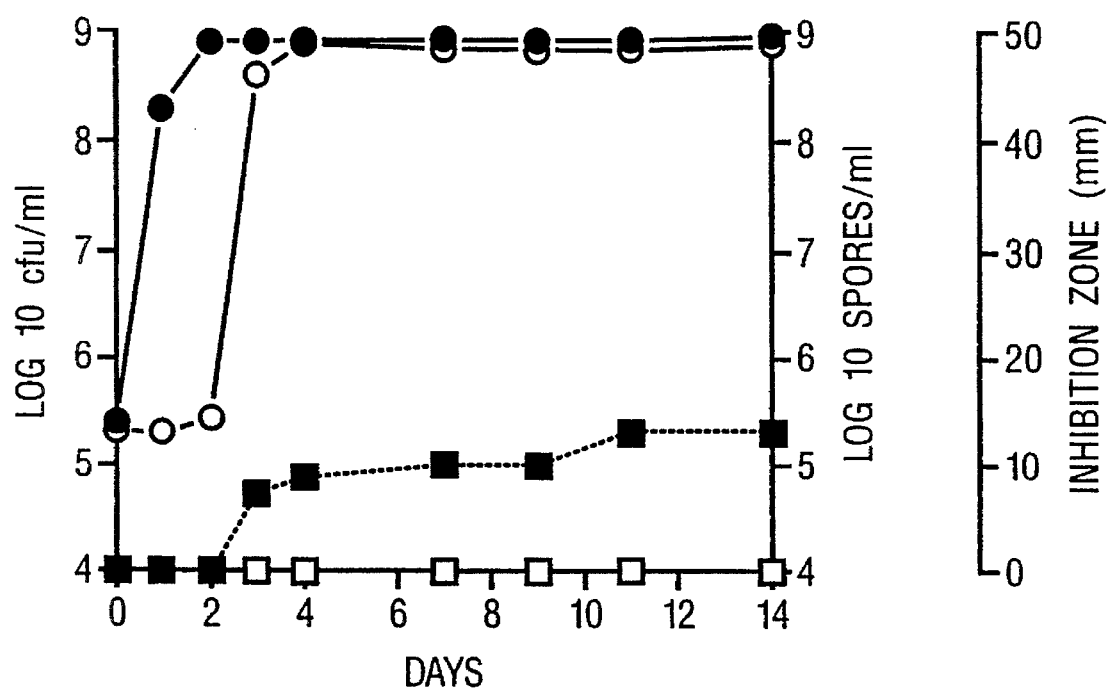
Figure 7A:
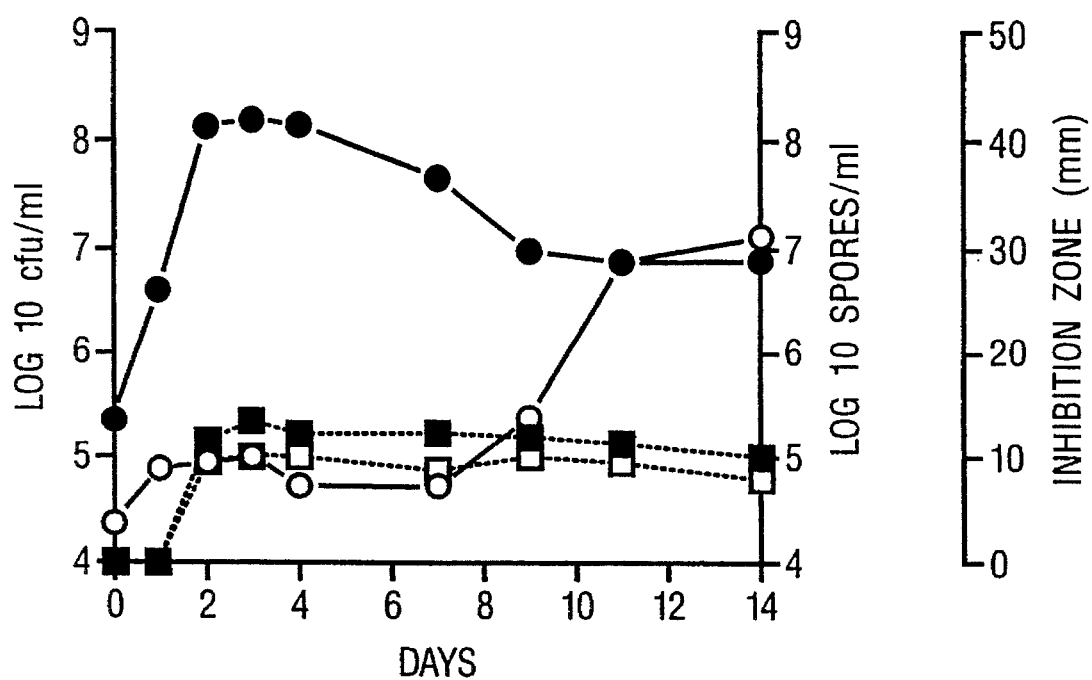
Figure 7B:
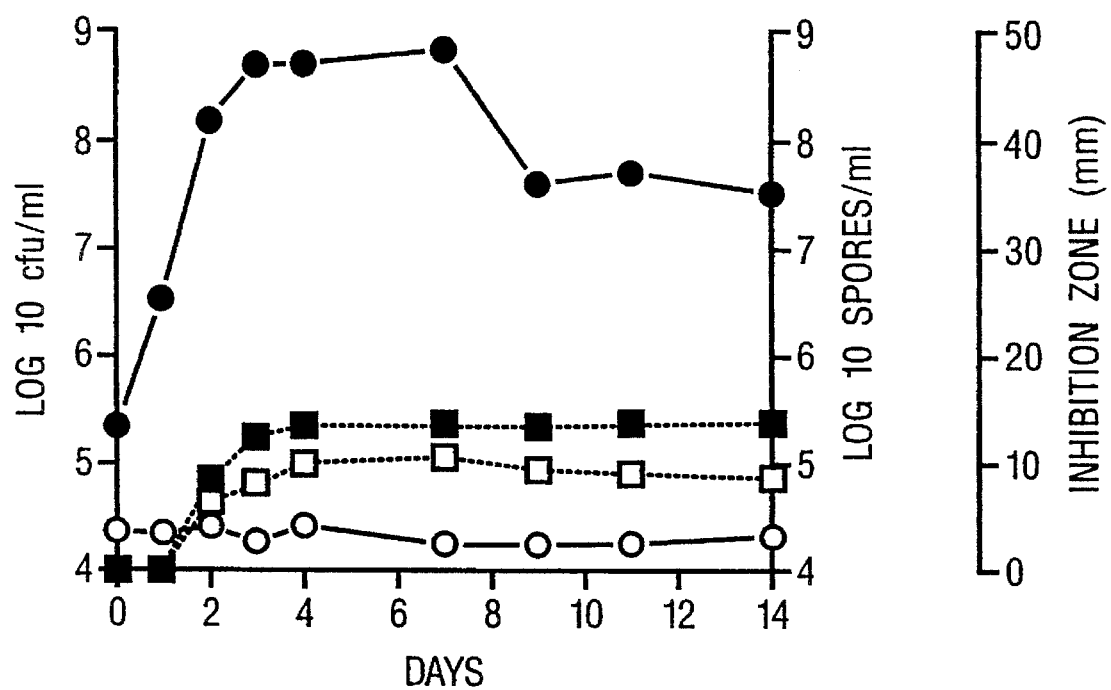

The production of antibiotics in batch culture after different incubation times and on different liquid media (NB, NB+Mn, NB+1% glucose, CA5, CA10, DM and DM+1% glucose) was studied. Culture filtrates of CL27 and CL45 again developed very strong activity (inhibition zones of around 40 mm) against *B. cinerea* when grown in cabbage broth (FIGS. 3 & 4), but developed much lower activity (inhibition zones <15 mm) when grown in nutrient broth (FIGS. 5 & 6) or defined media (FIG. 7). In cabbage broth (CA5 & CA10) both CL27 and CL45 developed anti-Botrytis activity after 2 days, approximately 24 hrs before the first newly formed Bacillus spores could be detected. On NB and DM antibiotic activity also developed after 2 days but an increase in the number of spores could only be detected after 9 days. Addition of 1% glucose inhibited Bacillus spore formation but not the development of antifungal activity in NB and DM (FIGS. 5 & 7).

As before, isolate CL27 but not CL45 developed activity against *Alternaria brassicicola*. Activity was highest in cell free culture filtrates from NB+Mg and CB10 batch cultures (20 mm inhibition zones) and similar in all other media (inhibition zones of between 15 and 10 mm) (FIGS. 3 to 7). Similar to the activity against Botrytis, anti-Alternaria activity preceded spore formation by 24 h in CA5 and CA10 and 7 days in NB and DM while addition of 1% glucose did not stop the development of antifungal activity (FIGS. 3 to 6).

EXAMPLE 7

Effect of pH and Nutrients on Antibiotic Activity

Figure 8A:
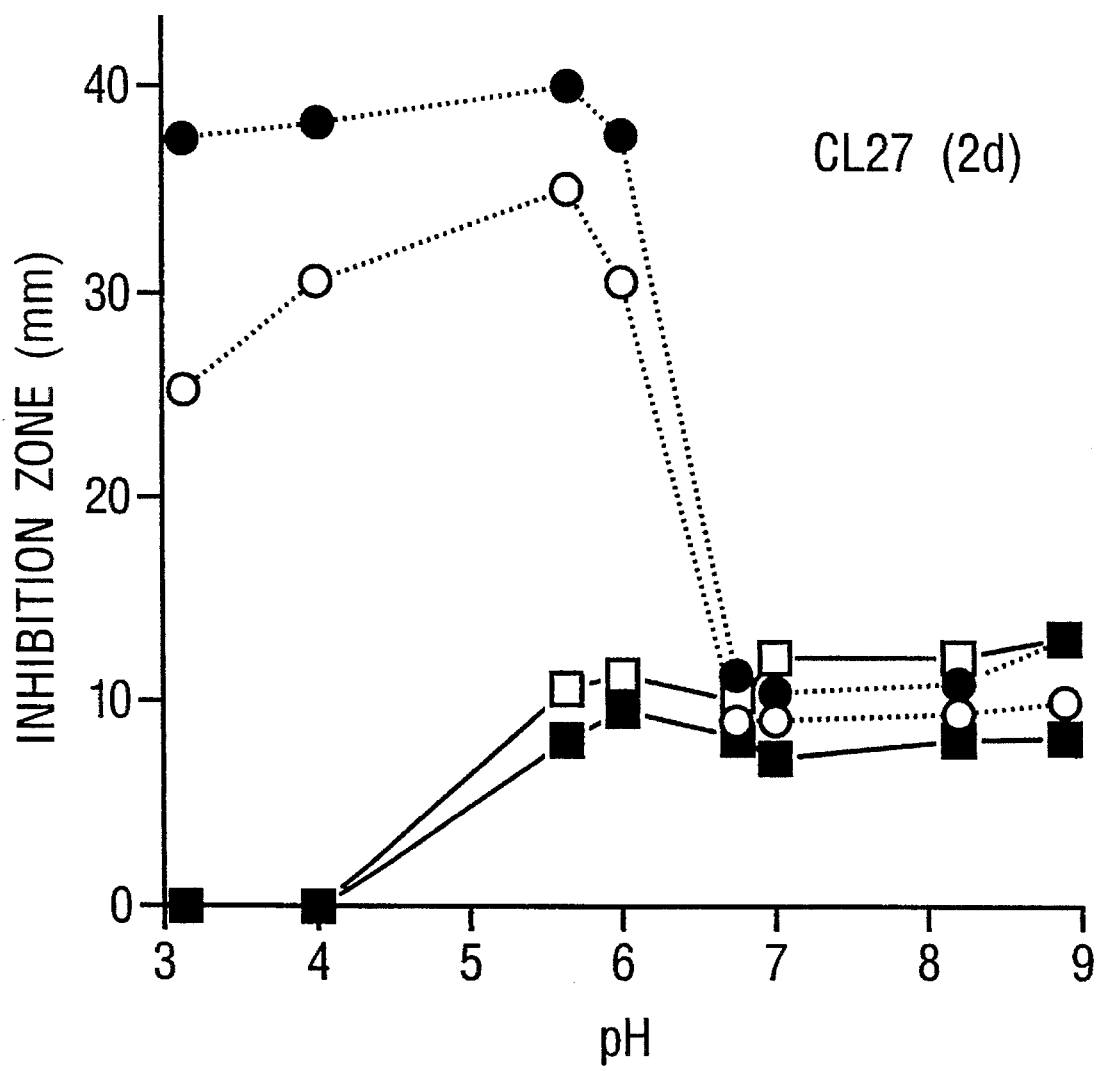
Figure 8B:
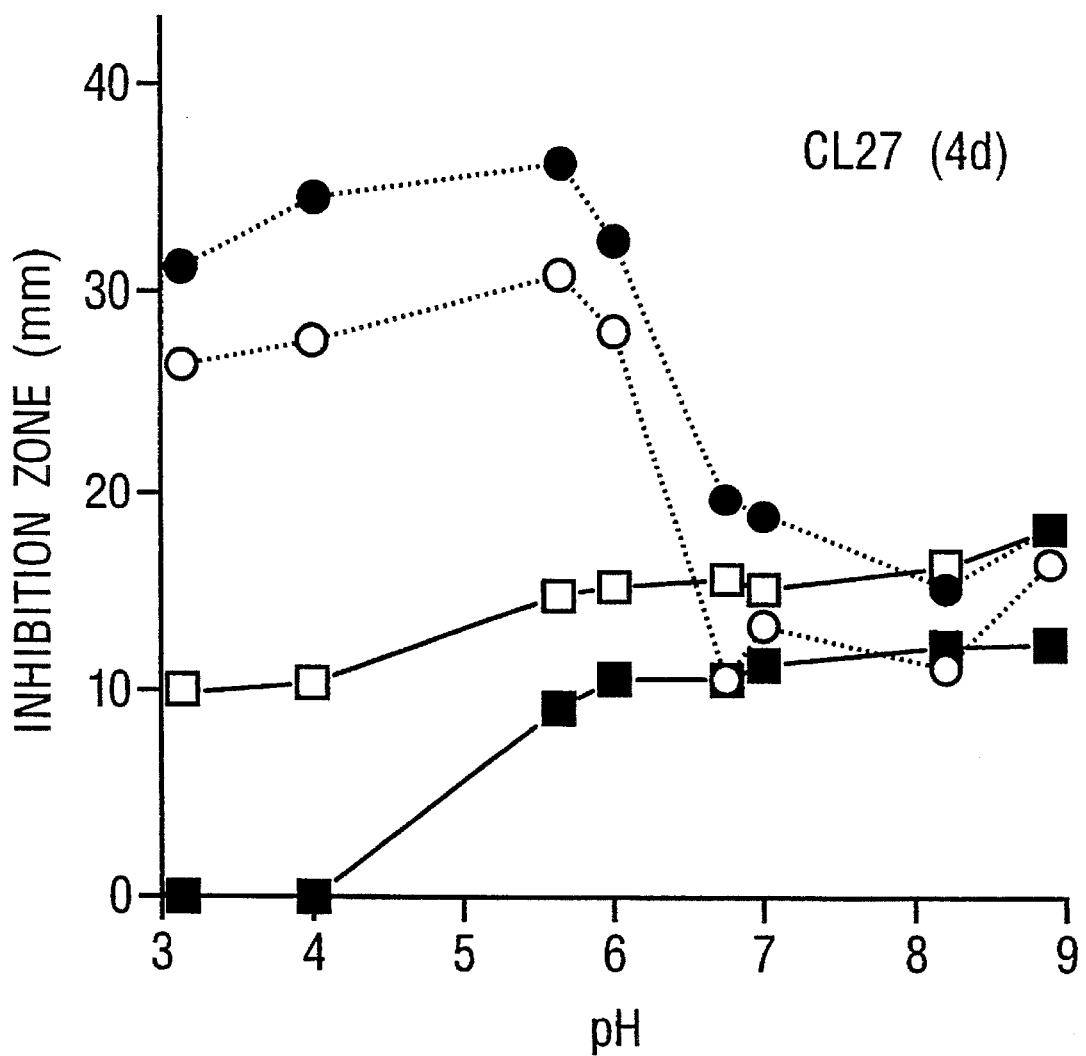
Figure 8C:
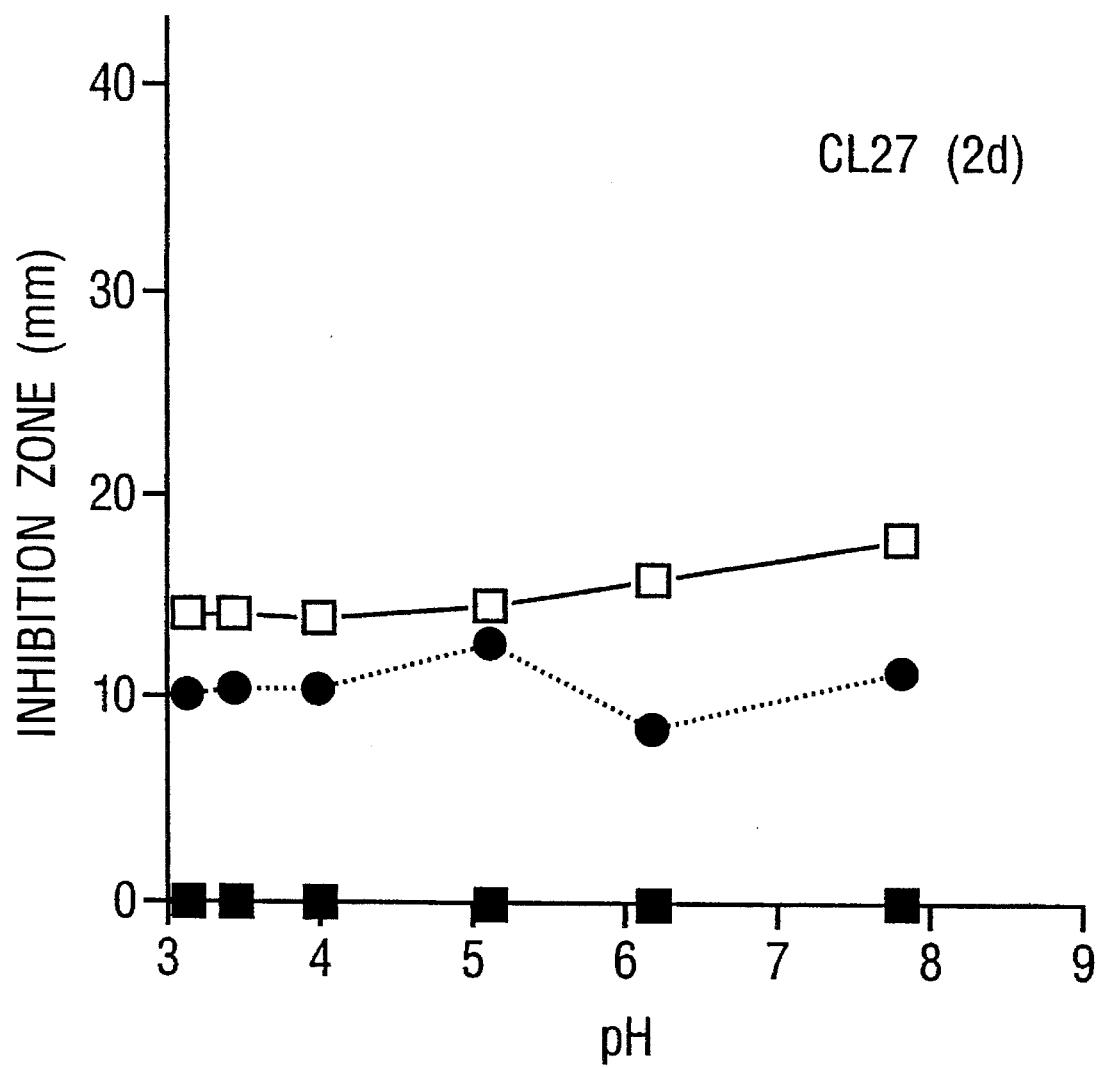
Figure 8D:
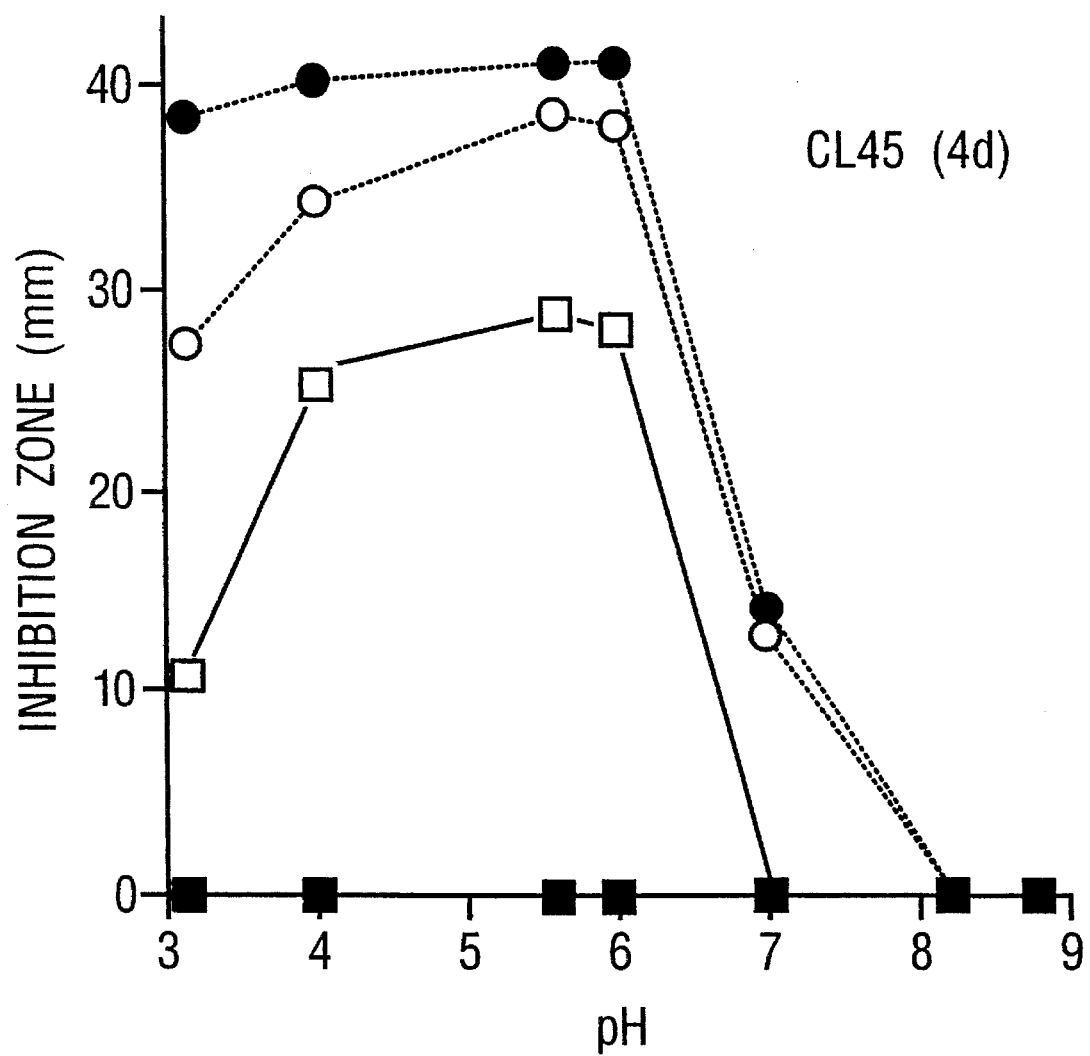
Figure 9:
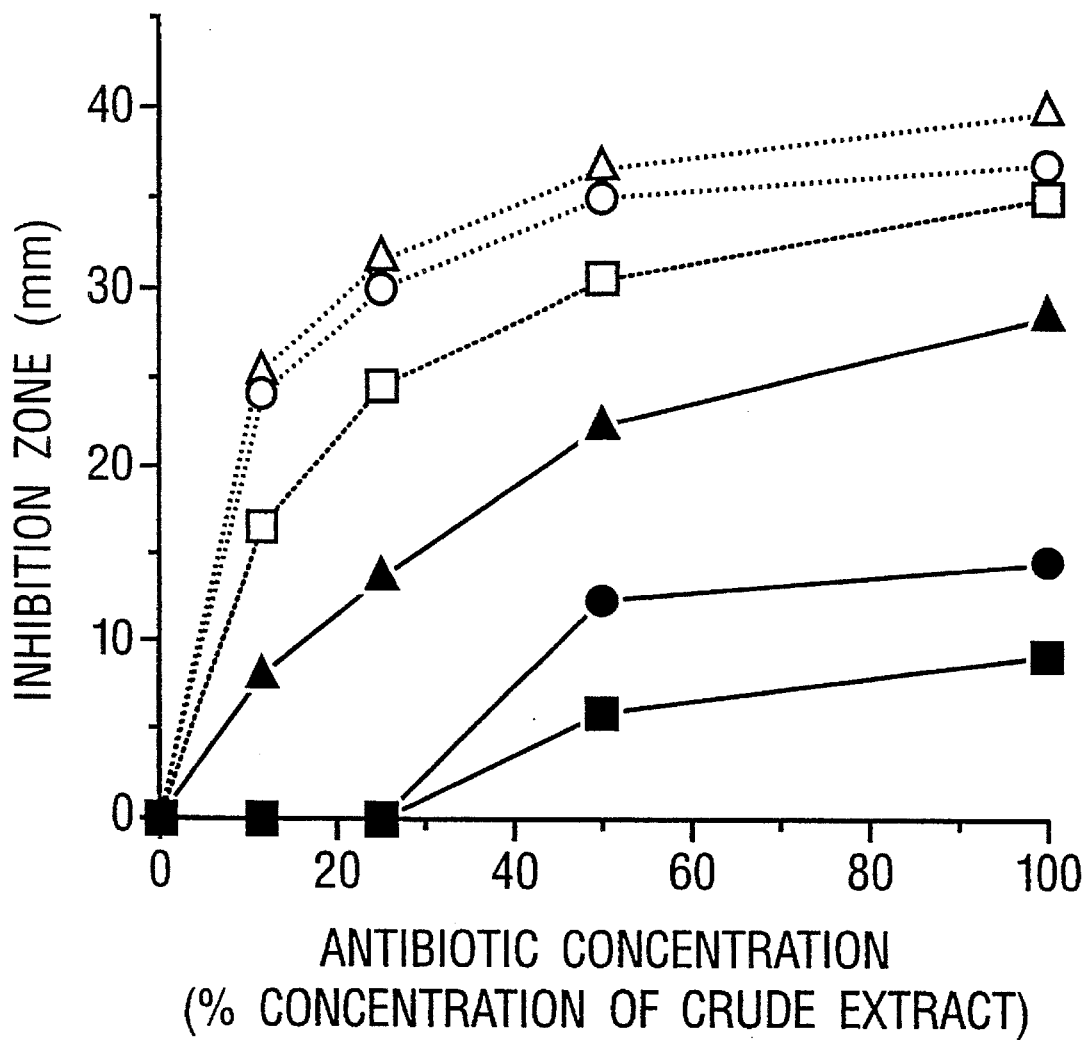

The activity of antifungal antibiotics formed in liquid batch culture of *Bacillus subtilis* (measured as the inhibition zone diameter on fungal seeded CA5 medium) was affected by the pH (FIG. 8) and the concentration and type of nutrients in the assay medium (FIG. 9).

pH Effects: Antibiotics produced in cabbage broth (CB5 & CB10) after 2 and 4 days and by CL45 in NB+Mg after 2 days showed the highest activity (formed the largest inhibition zones) against Botrytis between pH 5.6 and 6.0. Activity decreased slightly when the pH was reduced to 3.1 and to very low values when the pH was increased to values above 6.0 (FIG. 8). Antibiotics produced by CL27 on NB+Mg had similar activity between pH 5.6 and 8.9, but decreased activity when the pH was lower than 5.6. In NB activity could only be detected if the pH was above 6.0 and increased slightly with increasing pH. When antibiotic activity was assayed in Botrytis-seeded potato dextrose agar crude extracts from nutrient broth and CB5 showed no activity, extracts from CA10 showed lower activity at pH values below 6 but similar activity at higher pH and extracts from nutrient broth with manganese showed increased activity than on Botrytis-seeded cabbage agar used (FIG. 8C).

Nutrient levels: With increasing concentration of nutrients, in the form of cabbage tissue or potato extract and dextrose in the assay medium, the activity of antibiotics also decreased (FIG. 9). On Potato dextrose agar no, or only very small inhibition zones were formed (FIG. 9).

Stability of Antibiotics at Low Temperatures

Antibiotics formed were found to be very stable at 4° C. since no decrease in activity could be detected in the crude cell free culture filtrates of strains CL27, CL41 and CL45 stored sterile for 4 months. Filtrates were assayed at monthly intervals during storage at 4° C.

EXAMPLE 8

Isolation and Characterisation of Antibiotics Produced by *Bacillus subtilis* Strain CL27 and *Bacillis pumulis* Strain CL45

Bacteria were grown for 7 days in batch culture of either cabbage broth (10 g homgenized cabbage leaf tissue) or nutrient broth (+0.005 g Mn per liter). Cell free culture extracts were prepared as described above). 0.04 ml of the cell free culture filtrate was placed on Silica gel 60 TLC plates (Art. 5271; Merck) and separated using the solvent system described by Swinburne et al (Trans. Br. Mycol. Soc. 65 (2), 211–217) ie. Butan-1-ol: acetic acid: $H_2O$; 3:1;1. Plates were dried in a laminar flow cabinet then an oven for 5 hrs at 70° C. to remove solvent and acetic acid residues.

Fungal suspensions were made in either nutrient broth or cabbage broth (5 g/l homogenized cabbage leaves). The dried TLC plates were sprayed with spore suspensions of either *B. cineria* or *A. brassicicola* and incubated for 3 days or 4 days (depending on experiment) at 20° C. in darkness to allow fungal growth on the plates. Inhibition zones were visualised according to the methods of Lund & Lyon (J. Chromatography 100 192–196 (1975)) and used to calculate Rf values for the antibiotics produced.

| Antibiotic | Rf values |
| --- | --- |
| Cl27a Anti-Botrytis antibiotic produced in cabbage broth: Assumed non peptide (negative TDM): activity at pH <5.6. | 0.39 |
| CL27b Anti-Botrytis/Alternaria antibiotic produced in cabbage broth: Assumed peptide (positive TDM): activity at pH >5.6 | 0.56 |
| CL27c Anti-Alternaria antibiotic produced in nutrient broth Assunmed peptide nature (positive TDM): acitivity at pH >5.6. | 0.61 |
| CL45a Anti-Botrytis antibiotic produced in cabbage broth. Assumed non peptide (negative TDM): activity at pH <5.6. | 0.39 |

TDM=4,4'-tetramethyldiaminodiphenylmethane reagent: positive=blue/green. CL27 antibiotics are formed in Cabbage Broth (CB5), Nutrient Broth and Nutrient broth with manganese: CL45 antibiotics only Cabbage broth (CB5)

TABLE 7

| Fungus | Strain | CL27a | Cl27b | CL45a |
| --- | --- | --- | --- | --- |
| *Botrytis cinerea* | ST1, P19 | + | + | + |
| Trichocladium spp. | H7 | + | + | + |
| Phoma spp. | P13 | + | + | + |
| Zygorrhynchus spp. | P23 | – | + | + |
| Penicillium spp. | P5, I4 | – | + | – |
| Aspergillus spp. | P1 | – | + | – |
| Alternaria spp. | H9 | – | + | – |

TABLE 8

Dia. inhibition zones (mm) in fungal seeded media around well containing crude extracts of CL27 and CL45 broths: includes 3 mm well

| | | Bacillus subtilis | | | Bacillus pumilis | | |
| --- | --- | --- | --- | --- | --- | --- | --- |
| Genera | Strain | CA5/2D | CA5/4d | NB/4d | CA5/4d | NB/4d | d = day |
| Aspergillus | P1 | 0 | 8 | 8 | 0 | 0 | |
| | H9 | 0 | 4 | 4 | 0 | 0 | |
| Alternaria | OUT3 | 0 | 17 | 17 | 0 | 0 | |

TABLE 8-continued

Dia. inhibition zones (mm) in fungal seeded media around well
containing crude extracts of CL27 and CL45 broths: includes 3 mm well

| Genera | Strain | Bacillus subtilis | | | Bacillus pumilis | | |
|---|---|---|---|---|---|---|---|
| | | CA5/2D | CA5/4d | NB/4d | CA5/4d | NB/4d | d = day |
| Botrytis | P19 | 27 | 15 | 10 | 34 | 0 | |
| | C1 | 21 | 14 | 9 | 24 | 0 | |
| | MP3 | 30 | 19 | 12 | 28 | 0 | |
| | MP5 | 12 | 8 | 12 | 26 | 0 | |
| | G3/2 | 22 | 14 | 9 | 26 | 0 | |
| | ST1 | 10 | 10 | 9 | 30 | 0 | |
| Debaryomyces | P27 | 0 | 0 | 6 | 0 | 0 | |
| Penicillium | P5 | 0 | 0 | 8 | 0 | 0 | |
| | I4 | 0 | 0 | 11 | 0 | 0 | |
| | M4 | 0 | 0 | 0 | 0 | 0 | |
| | PR5 | 0 | 0 | 7 | 0 | 0 | |
| Phoma | P13 | 0 | 5 | 6 | 5 | 0 | |
| Trichocladium | H7 | 6 | 5 | 14 | 0 | 0 | |
| Trichphyton | C3 | 0 | 0 | 11 | 0 | 0 | |
| Trichosporum | P29 | 31 | 12 | 0 | 46 | 0 | |
| Zygorrhynchus | P23 | 0 | 0 | 23 | 20 | 0 | |
| Rhodotorula | G4/1 | 0 | 0 | 0 | 0 | 0 | Yeast |
| Cryptococcus | G4/6 | 0 | 0 | 8 | 0 | 0 | Yeast |

When TLC plates on which cell free culture filtrates from CB5 medium inoculated with either CL27 or C145 were over layered with *Botrytis cinerea* seeded medium large inhibition zones (30–40 mm) developed at an rf of 0.38 to 0.40. When filtrates from CB5 medium inoculated with strain CL27 were examined an additional small band (3 mm) without fungal growth could be detected at an rf-value of 0.56 (not present when CB5 inoculated C45 was tested). When filtrates from NB and NB+Mn inoculated with CL45 were overlayed in this manner, only a small band of inhibition with an rf-value of 0.56 could be detected (there were no zones of inhibition when NB and NB+Mn medium inoculated with CL-45 were examined).

When the overlaying was carried out against *Alternaria brassicocola* seeded medium, 2 inhibition zones were detected (rf 0.56 and 0.61) from NB, NB+Mn and CB5 CL27 growth media inoculations. Thus it is seen that CL27 at least three antibiotics; one active against *B. cinerea* (rf. 0.39) only produced on cabbage extract and active at pH less than 6; one weakly active against *B. cinerea* and active against *A. brassicocola* (rf 0.56) produced on all media tested and active above pH 5.6; and a third active only against *A. brassicocola* (rf 6.1) again produced on all media tested. The similar rf value for the CL45 and CL27 antibiotics suggest that they are the same, but activity patterns suggest the opposite.

TABLE 9

In vitro inhibition (Petri dishes) of *Botrytis cinerea* by
Bacillus spp. isolated from Brassica spp.; mean 3 determinations.

| Isolate code | Origin | Isolation Medium | Inhibition zone diameter (mm) at 20° C. on Botrytis seeded cabbage medium Concentration of nutrients (g/l) | | | |
|---|---|---|---|---|---|---|
| | | | 100 | 50 | 10 | 5 |
| *B. subtilis* | | | | | | |
| CL0027 | BRL | NA | 24 | 30 | 0 | 0 |
| CL0041 | DWL | CA5 | 24 | 30 | 0 | 0 |
| CL0048 | " | SA | 22 | | | |
| CL0052 | " | PDA | 21 | | | |

TABLE 9-continued

In vitro inhibition (Petri dishes) of *Botrytis cinerea* by
Bacillus spp. isolated from Brassica spp.; mean 3 determinations.

| Isolate code | Origin | Isolation Medium | Inhibition zone diameter (mm) at 20° C. on Botrytis seeded cabbage medium Concentration of nutrients (g/l) | | | |
|---|---|---|---|---|---|---|
| CL0055 | DWLo | SA | | 29 | | |
| CL0056 | " | " | 34 | | | |
| CL0063 | " | " | 28 | | | |
| CL0071 | " | PDA | 24 | | | |
| *B. pumilis* | | | 100 | 50 | 10 | 5 (g/l) |
| CL0045 | DWL | CA5 | 26 | 34 | 0 | 0 |
| CL0064 | DWLo | SA | | 10 | | |
| CL0069 | | PDA | 21 | | | |
| *B. polymyxa* | | | | | | |
| CL0047 | DWL | SA | | 10 | | |
| CL0067 | DWLo | SA | 19 | | | |
| CL0068 | | PDA | 18 | | | |

- no visible bacterial growth BRL Broccoli leaves BSL Brussel's sprout

TABLE 10

Inhibition zones (mm on Petri dishes) formed by cell free
culture filtrates of Bacillus spp. of lawns of *A. brassicicola*
and *B. cinerea* (mean is of 2 determinations; Bacillus spp.
were grown for 5 days in the medium)

| Bacterial strain | Culture medium | | | |
|---|---|---|---|---|
| | Nutrient broth | | Cabbage broth | |
| | Alternaria | Botrytis | Alternaria | Botrytis |
| CL0008 | 6 | 0 | 2 | 20+ |
| CL0019 | 8 | 0 | 2 | 30+ |
| CL0020 | 6 | 0 | 2 | 8+ |
| CL0025 | 7 | 0 | 0 | ND |
| CL0026 | 6 | 0 | 4 | 22+ |
| CL0027 | 6 | 0 | 14 | 20 |
| CL0027 | 12* | 10* | 20* | 31* |
| CL0028 | 6 | 0 | 4 | 10 |

TABLE 10-continued

Inhibition zones (mm on Petri dishes) formed by cell free culture filtrates of Bacillus spp. of lawns of *A. brassicicola* and *B. cinerea* (mean is of 2 determinations; Bacillus spp. were grown for 5 days in the medium)

| Bacterial strain | Culture medium | | | |
|---|---|---|---|---|
| | Nutrient broth | | Cabbage broth | |
| | Alternaria | Botrytis | Alternaria | Botrytis |
| CL0041 | 6 | 0 | 10 | 19 |
| | 13* | 11* | 20* | 30* |
| CL0045 | 0 | 0 | 0 | 35 |
| | 0* | 9* | 0* | 45* |

*Sens-acute (Proteus) trasy; + = some fungal growth

EXAMPLE 9

Characteristics of Antagonistic Bacterial Isolates of the Invention

All bacterial strains isolated from Brassica spp. showing in vitro antagonism against *Botrytis cinerea* were found to be *Pseudomonas fluorescens* (group 1), Bacillus or Serratia species. Fluorescent pseudomonads and Enterobacteriaceae have been found to be the major inhabitants of cabbage leaves while Bacillus spp. were only found in very low numbers on Brassica leaves. Fluorescent pseudomonads and Bacillus spp. have previously been described as potential biocontrol agents against post-harvest fungal diseases of fruit and vegetables, whereas *Serratia plymuthica* and *Serratia liquefaciens* have not previously been shown to have such activity (see Wilson & Wisniewski 1989 for a recent review on biocontrol of post-harvest fungal diseases of fruit and vegetables).

*Pseudomonas fluorescens*

Fluorescent pseudomonad strains CL42, CL66 and CL82 of all bacterial strains tested showed the highest in vivo activity on leaf disks at 4° C., inhibiting Botrytis infection with all fungal inocula tested. Pseudomonads such as *P. cepacia. P. putida.* and *P. syringae* have been described as post-harvest biocontrol agents for a variety of stored fruit and vegetables and their mode of action has been described as being either by antibiotic production or by nutrient competition (Colyer & Mount 1984, James & Gutterson 1986, Gurusiddaiah et al. 1986, Janisiewicz 1987, Janisiewicz & Roitman 1988). It is important to note that *P. syringae* and *P. cepacia* can be pathogenic to plants and that some pseudomonads including *P. sceptical* have been described as opportunistic human pathogen (Agrios 1988, Bergan 1981).

Some of the antagonistic pseudomonads isolated by the present inventors were also found to be pathogenic to some vegetables eg. cabbages. Antagonistic pseudomonads should therefore be identified to species level to avoid using possible human pathogens and tested for effect on plants before use as postharvest control agents. Because the antagonistic strains isolated were able to persist on cabbage leaves they qualify as ideal potential candidates for biocontrol during storage of Brassica spp.

Serratia spp.

Serratia spp. isolated from cabbage leaves grew well and showed strong in vitro antagonism at low temperatures. However, only *S. plymuthica* strain CL42 showed high in vivo antagonism against *B. cinerea* on leaf disks. All *S. liquefaciens* strains showed intermediate to poor control 'in vivo'. Serratia spp. have not previously been identified as fungal antagonists. Serratia spp. have not been described as plant pathogens but *S. marcescens* has been described as causing human nosocomial infection (Brenner 1984). Such organisms should therefore only be used once they have been shown to be non-pathogenic to man. Enterobacteriaceae form a major part of the natural flora of cabbage leaves and because the antagonistic strains isolated were able to persist on cabbage leaves they have potential as biocontrol agents, eg. particularly during storage of Brassica spp.

Bacillus spp.

Bacillus spp. are considered to be unsutiable as potential biocontrol agents for cold-storage since they did not grow or grew very poorly at low temperatures. This has not been reported before because most workers describing the use of Bacillus species for post-harvest biocontrol of fungal pathogens of fruit and vegetables have only tested 'in vitro' and 'in vivo' antagonism at temperatures of around 200C (Pursey & Wilson 1984, Singh & Deverall 1984, Utkhede & Sholberg 1986, Gueldner et al. 1988). Their poor growth at low temperatures could, however, be the explanation for variable results described in the field and in pilot tests for commercial application of *Bacillus subtilis* based biocontrol agents (Baker et al. 1985; Pusey et al. 1986 & 1988). Bacillus spp. are known to produce peptide antibiotics with antifungal activity during spore formation (see Katz & Demain 1977 for a review) and peptide antibiotics have been identified as the active compounds in the use of *Bacillus subtilis* as a biocontrol agent for post-harvest fungal diseases (McKeen et al. 1986, Gueldner et al. 1988).

Production of such antibiotics by fermentation and their use as 'bio-pesticides' is the preferred use of such Bacillus if no cold resistant antagonistic Bacillus spp. is isolable. However the antibiotics and the organisms might also be used to prolong the shelf-life when fruit and vegetables are removed from the cold-store. The poor activity of crude antibiotic extracts when assayed in potato dextrose agar (PDA) indicates that the antibiotics found are novel, since PDA has been used by most other authors to select Bacillus spp. which produce anti-fungal antibiotics (Katz & Demain 1977; Pusey & Wilson 1984; Singh & Deveral 1984; McKeen et al. 1986; Utkhede & Sholberg 1986; Wilson & Wisniewski 1989).

Details of all the strains of the invention are provided in Tables 11 and 12.

EXAMPLE 10

In vivo Activity of all Strains Against *B. cinerea* on Young Plant Leaf Surfaces CL82, CL80 and CL27 were tested for ability to control *B. cinerea* on leaf surfaces in vivo using a young plant assay in high humidity propagation chambers. Only CL27 showed significant control, similar to that achieved by fungicides. Application of cell free culture filtrates of the CL27 broth gave similar control to that provided by the cell suspension, thus indicating an antibiotics effect. This result shows that CL27 and its derivatives can be used as bio-control agent applied before harvest. In order to determine the effectiveness of such an application after harvest, persistence studies were carried out.

Astilbe microplants were planted into 3×3 cm compost plugs and sprayed at weekly intervals with fungal spores and antagonists in a humidity of 86% to 95%. For the first 6 weeks all treatments gave similar success, but after 10 weeks only fungicide and treatment using CL27 or its broth gave significant control. CL27 returned better control than fungicide in these tests.

EXAMPLE 11

Effect of Serratia and Pseudomonas Strains on Stored Produce

Dutch white cabbages (var. Morgan) were grown and treated with insecticide and herbicides in the normal fashion, but not fungicides. After harvest cabbages were dipped in either fungicide suspension (1 g/l Rovral and 2 g/l Ridomil) or into bacterial suspensions of $10^7$ to $10^8$ cfu/ml. Approx. 14 kg cabbage (10–12 heads) were transferred into plastics trays and sealed in plastics to avoid cross-contamination; 5 replicate trays were used for each treatment. Trials were set up in a cold store at 4°–6° C. and at 1°–3° C. with humidity measured at 7 day intervals and found to be 92 to 96% in all cases. In one of the trials $10^6$ spores/ml B. cinerea were applied after the fungicides or bacteria; 5 ml spore suspension sprayed onto each tray.

Cabbages were scored as follows: 0=no visible growth; 1=1–10%, 2=11–25%, 3=26–50%, 4=51–75%, 5=76–90%, 6=91–99%, 7=100% of surface covered by fungal growth and measured at 6 weekly intervals. When 80% coverage occurred in the untreated controls (when trimming occurs in commercial storage) destructive assessment was made by reference to weight loss on removal of infected leaves. Heads were stored again for 10 to 14 weeks and then trimmed after 42 weeks. Trial at 1°–3° C. did not allow destructive testing so extrapolation of leaf infected area with trimming loss was carried out.

Use of CL80 and CL82 gave control similar to that of fungicides in all cases, CL82 giving better inhibition in added B. cinerea treatment than A. brassicicola; the opposite of in vitro results. CL82 persisted on cabbage in higher numbers than other antagonists and thus is a preferred example of the invention. Of the other strains, CL43 was the most efficacious in cold store.

TABLE 11

Characteristics of antagonistic Pseudomonas and Serratia spp.

| Characteristics | Pseudomonas fluorescens (group 1) | Serratia Plymuthica | Serratia liquefacien |
|---|---|---|---|
| Gram stain | − | − | − |
| Hugh & Leifson | − | + | + |
| Motility | + | + | + |
| Fluorescence on KB-agar | + | − | − |
| Oxidase | + | − | − |
| Beta-galactosidase | − | + | + |
| Arginine dihydrolase | +* | − | − |
| Lysine decarboxylase | ND | − | + |
| Ornithine decarboxylase | ND | − | − |
| Citrate utilisation | ND | + | + |
| H₂S production | ND | − | − |
| Urease | − | − | − |
| Esculin hydrolysis | −1 | ND | ND |
| Tryptophan deaminase | ND | − | − |
| Indole production | − | − | − |
| Acetoin production | ND | + | + |
| Gelatine hydrolysis | + | + | + |
| NO₃-reduction | + | + | + |
| Growth on: | | | |
| Glucose | + | +& | +& |
| Mannitol | + | + | + |
| Inositol | ND | +* | − |
| Sorbitol | ND | + | + |
| Rhamnose | ND | − | − |
| Sucrose | ND | +% | +% |
| Melibiose | ND | + | + |
| Amygdalin | ND | + | + |
| Arabinose | + | + | + |
| Mannose | + | ND | ND |
| N-Acetylglucosamine | + | ND | ND |
| Maltose | − | ND | ND |
| Gluconate | + | ND | ND |
| Caprate | + | ND | ND |
| Adipate | − | ND | ND |
| Malate | + | ND | ND |
| Citrate, | + | ND | ND |
| Phenyl-acetate | − | ND | ND |
| Raffinose3 | ND | ND | + |
| Manolate3 | ND | ND | − |
| Lactose3 | ND | ND | − |
| Adonitol3 | ND | ND | − |

&positive after 6 h
*positive after 48 h
+positive test result
−negative test result
ND not determined
1 isolates CL74, positive
2 Serratia spp. were tested for acidification from carbohydrates
3 additional tests (Brenner 1984)

TABLE 12

Characteristics of antagonistic Bacillus subtilis Bacillus pumilus and Bacillus polymyxa spp.

| Characteristics | Bacillus subtilis CL27, 41, 48, 52 55, 56, 63, 71 | Bacillus pumilus CL45, 64, 69 | Bacillus polymyxa CL47, 67, 68 |
|---|---|---|---|
| Gram stain | + | + | + |
| Motility | + | + | + |
| Heat resistant spores | + | + | + |
| Beta-galactosidase | + | + | + |
| Arginine dihydrolase | − | − | − |
| Lysine decarboxylase | − | − | − |
| Ornithine decarboxylase | − | − | − |
| Citrate utilisation | V1 | V1 | − |
| H₂S production | − | − | − |
| Urease | − | − | − |
| Tryptophan deaminase | − | − | − |
| Indole production | − | − | − |
| Acetoin production | + | + | + |
| Gelatin hydrolysis | + | + | + |
| NO₃-reduction | + | + | + |
| Acid from: | | | |
| Glycerol | + | + | + |
| Erythritol | − | − | − |
| D-Arabinose | − | − | − |
| L-Arabinose | + | + | +g |
| Ribose | + | + | +g |
| D-Xylose | + | + | +g |
| L-Xylose | − | − | − |

TABLE 12-continued

Characteristics of antagonistic Bacillus subtilis Bacillus pumilus and Bacillus polymyxa spp.

| Characteristics | Bacillus subtilis CL27, 41, 48, 52 55, 56, 63, 71 | Bacillus pumilus CL45, 64, 69 | Bacillus polymyxa CL47, 67, 68 |
|---|---|---|---|
| Adonitol | − | − | − |
| β-Methyl-xyloside | − | − | + |
| Galactose | V2 | + | +g |
| D-Glucose | + | + | +g |
| D-Fructose | + | + | +g |
| D-Mannose | + | + | +g |
| L-Sorbose | − | − | − |
| Rhamnose | − | − | − |
| Dulcitol | − | − | − |
| Inositol | + | − | − |
| Mannitol | + | + | +g |
| Sorbitol | + | − | − |
| alpha-Methyl-D-mannoside | − | V3 | + |
| alpha-Methyl-D-glucoside | + | − | + |
| N-Acetyl glucosamine | − | + | − |
| Amygdaline | + | + | +g |
| Arbutine | + | + | + |
| Esculine | + | + | + |
| Salicine | + | + | +g |
| Cellobiose | + | + | +g |
| Acid from: | | | |
| Maltose | + | V4 | +g |
| Lactose | − | V5 | +g |
| Melibose | + | V6 | +g |
| Sucrose | + | + | +g |
| Trehalose | + | + | +g |
| Inuline | + | − | +g |
| Melezitose | − | − | − |
| D-Raffinose | + | V7 | +g |
| Amidon | + | − | +g |
| Glycogene | + | − | +g |
| Xylitol | − | − | − |
| β-Gentiobiose | V8 | + | + |
| D-Turanose | V9 | V9 | + |
| D-Lyxose | − | − | − |
| D-Tagatose | − | + | − |
| D-Fucose | − | − | − |
| L-Fucose | − | − | − |
| D-Arabitol | − | − | − |
| L-Arabitol | − | − | − |
| Gluconate | −p | − | + |
| 2-ceto-gluconate | − | − | −p |
| 5-ceto-gluconate | − | − | − |

+ positive test result
− negative test result
V variable test result

1 CL27,45,52,56,63 negative, CL41,48,55,64,69,71 positive

2 CL27,41,48,52,55,56,71 negative; C163 positive

3 CL45 negative; CL64,69 positive

4 CL64,69 negative; CL45 positive

5 CL45,69 negative; CL64 positive

6 CL45 negative; CL64,69 positive

7 CL45 negative; CL64,69 positive

8 CL41 negative; CL27,48,52,55,56,63,71 positive

9 CL27,41,48,63,64,69 negative; CL45,52,55,56,71 positive

REFERENCES

Agrios, G. N. (1988) *Plant Pathology.* New York: Academic Press.
Baker, C. J. et al (1983) *Plant Disease.* 69, 770–772.
Bergan, T. (1981) in *The Prokaryotes Vol. I,* ed. Starr et al, pp. 666–701.
Brenner D J (1981) in *The Prokaryotes Vol. II.* ed. Starr et al pp.1103–1128.
Brenner, D. J. (1984) *Bergey's Manual of Systematic Bacteriology* (9th Edition) (Ed. by Krieg, N. R. & Holt, J. G.), pp. 408–420.
Williams and Wilkins, Baltimore.
Brown, A et al (1975) *Proc 8th.Brit.Insecticide/Fungicide Conf* 1, 339–346.
Colyer, P. D. & Mount, M. S. (1984) *Plant Disease.* 68, 703–706.
Dickinson, C. H. & Preece (1976) Microbiology of aerial plant surfaces. Academic Press, London.
Geeson, J. D. (1978) *Grower.* 89, 27–31.
Gueldner, R. C et al (1988) *J. Agricultural and Food Chem.* 36, 366–370.
Gurusiddaiah, S. et al (1986) *Antimicrob. Ag. and Chemotherapy,* 29, 488–495.
Hampson, S. B. et al (1991) *Letters of Applied Microbiology*
Howell, C. R. et al, (1988) *Phytopathology,* 78, 1075–1078.
James, D. W. et al (1986) *Appl. and Environmental Microbiol.* 52, 1183–1189
Janisiewicz, W. J. (1987) *Phytopathology,* 77, 481–485.
Janisiewicz, W. J. et al (1988) *Phytopathology,* 78, 1697–1700.
Katz, E. et al (1977) *Bacteriological Reviews.* 41, 449–474.
Leifert, C. et al (1992) *Letters of Applied Microbiology*
McKeen, C. D., et al (1986) *Phytopathology.* 76, 136–139.
Newhook, F. J. (1951) *Annals of Microbiology.* 38, 169–184.
Pusey, P. L. et al (1984) *Plant Disease.* 68, 753–56.
Pusey, P. L. et al (1986) *Plant Disease.* 70, 587–590.
Pusey, P. L. et al (1988) *Plant Disease.* 72, 622–626.
Robinson, D. H. et al (1975) *Annals of Applied Biology.* 81, 339 408.
Singh, V. et al (1984) *Transcripts of Brit. Mycological Soc.* 83, 487–490.
Spotts, R. A. et al (1986) *Plant Disease.* 70, 106–108.
Utkhede, R. S. et al (1986) *Canadian J. of Microbiology.* 32, 963–967.
Wale, S. J. (1980) The post-harvest pathology of Dutch white cabbage in refrigerated storage. Ph.D. Thesis, Manchester University.
Wilson, C. L et al (1989) *Annual Review of Phytopathology.* 27, 425–441.
Wisniewski, M. (1989) *Canadian Journal of Botany.* 67, 2317–2323.

We claim:

1. A process of producing an antibiotic comprising the steps of:

(a) providing a source of bacteria isolates having all the identifying characteristics of an isolate selected from the group consisting of *Bacillus subtilis* NCIMB 40489 and *Bacillus pumulis* NCIMB 40491, said isolate having the characteristic of inhibiting growth of *Alternaria brassicola* or *Botrytis cineria* or both on cabbage leaves at temperature of about 20° C.;

(b) culturing said bacteria isolates in a broth of homogenized cabbage leaves and water in a concentration of between 5 g and 100 g leaves per liter until a sufficient amount of the antibiotic has been accumulated; and thereafter (c) recovering the antibiotic so produced.

2. The process as claimed in claim 1, wherein said broth is of concentration 10 g to 50 g leaves per liter.

3. The process as claimed in claim 1, wherein in step (c) the product culture medium is filtered to remove cells, the filtrate is dewatered and the residue separated using a silica gel column or plate with a butan-1-ol:acetic acid:water; 3:1:1 eluant.

4. The process as claimed in claim 3, wherein on separating the residue using a silica gel plate and butan-1-ol:acetic acid:water; 3:1:1 eluant, said antibiotic has an Rf value of about 0.39.

5. The process as claimed in claim 3, wherein on separating the residue using a silica gel plate and butan-1-ol:acetic acid:water; 3:1:1 eluant, said antibiotic has an Rf value of about 0.56.

6. A process of producing an antibiotic comprising the steps of:
   (a) providing a source of bacteria isolate having all the identifying characteristics of *Bacillus subtilis* NCIMB 40491;
   (b) culturing said isolate in a nutrient broth until a sufficient amount of the antibiotic has accumulated;
   (c) filtering the product culture medium to remove cells; and
   (d) dewatering the filtrate, wherein on separating the residue using a silica gel plate and butan-1-ol; acetic acid:water; 3:1:1 eluant, said antibiotic has an Rf value of about 0.61.

7. An antibiotic composition produced by the process of claim 1 containing cell free antibiotics cultured from bacteria isolates having all the identifying characteristics of an isolate selected from the group consisting of *Bacillus pumulis* NCIMB 40489 and *Bacillus subtilis* NCMB 40491, said isolates sharing the characteristic of inhibiting growth of *Alternaria brassicola* or *Botrytis cineriea* or both on cabbage leaves at temperature of about 20° C.

8. A method of inhibiting post harvest disease comprising applying an effective amount of the antibiotic composition as claimed in claim 7 to crops or plants susceptible to post harvest disease.

* * * * *